(12) United States Patent
Lindsay

(10) Patent No.: US 12,276,653 B2
(45) Date of Patent: Apr. 15, 2025

(54) BIOELECTRONIC DEVICES WITH PROGRAMMABLE ADAPTORS

(71) Applicant: Arizona Board of Regents on behalf of Arizona State University, Scottsdale, AZ (US)

(72) Inventor: Stuart Lindsay, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 993 days.

(21) Appl. No.: 17/333,087

(22) Filed: May 28, 2021

(65) Prior Publication Data

US 2021/0372986 A1 Dec. 2, 2021

Related U.S. Application Data

(60) Provisional application No. 63/125,674, filed on Dec. 15, 2020, provisional application No. 63/032,266, filed on May 29, 2020.

(51) Int. Cl.
  *G01N 33/487* (2006.01)
  *C12Q 1/00* (2006.01)
  *G01N 27/327* (2006.01)

(52) U.S. Cl.
  CPC ....... *G01N 33/48721* (2013.01); *C12Q 1/005* (2013.01); *G01N 27/3273* (2013.01)

(58) Field of Classification Search
  None
  See application file for complete search history.

(56) References Cited

U.S. PATENT DOCUMENTS

| | | | |
|---|---|---|---|
| 5,198,543 A | 3/1993 | Blanco | |
| 6,824,974 B2 | 11/2004 | Pisharody et al. | |
| 7,632,671 B2 | 12/2009 | Tong | |
| 8,628,649 B2 | 1/2014 | Lindsay et al. | |
| 8,961,757 B2 | 2/2015 | Nuckolls et al. | |
| 8,968,540 B2 | 3/2015 | Reinhart et al. | |
| 9,140,682 B2 | 9/2015 | Lindsay et al. | |
| 9,274,430 B2 | 3/2016 | Gyarfas et al. | |
| 9,376,713 B2 | 6/2016 | Bashir et al. | |

(Continued)

FOREIGN PATENT DOCUMENTS

| | | |
|---|---|---|
| CN | 104359946 | 2/2015 |
| JP | 2016188794 A | 11/2016 |

(Continued)

OTHER PUBLICATIONS

Lindsay. Ubiquitous Electron Transport in Non-Electron Transfer Proteins. Life (Basel). May 20, 2020;10(5):72. 13 pages.

(Continued)

*Primary Examiner* — J. Christopher Ball
(74) *Attorney, Agent, or Firm* — Casimir Jones, S.C.; Peter J. Schlueter

(57) ABSTRACT

The present disclosure provides devices, systems, and methods related to bioelectronic devices. In particular, the present disclosure provides bioelectronic devices, and methods of making bioelectronic devices, comprising adjustable adaptor polypeptides with repeatable motifs and enhanced conductive properties. The bioelectronic devices and methods of the present disclosure are useful for a variety of applications, including the direct measurement of protein activity (e.g., when sequencing a biopolymer).

35 Claims, 20 Drawing Sheets

Specification includes a Sequence Listing.

(56) References Cited

U.S. PATENT DOCUMENTS

| | | |
|---|---|---|
| 9,593,372 B2 | 3/2017 | Lindsay et al. |
| 9,938,586 B2 | 4/2018 | Liang et al. |
| 10,047,392 B2 | 8/2018 | Ivankin et al. |
| 10,051,722 B2 | 12/2018 | Jin et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0285275 A1 | 12/2005 | Son et al. |
| 2009/0215156 A1 | 8/2009 | Chung et al. |
| 2009/0226899 A1 | 9/2009 | Chen |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0312529 A1 | 12/2011 | He et al. |
| 2012/0228386 A1 | 9/2012 | Wu et al. |
| 2013/0302901 A1 | 11/2013 | Lindsay et al. |
| 2014/0141525 A1 | 5/2014 | Albert et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2016/0018384 A1 | 1/2016 | Lindsay et al. |
| 2016/0025702 A1 | 1/2016 | Lindsay et al. |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0137389 A1 | 5/2017 | Zhang et al. |
| 2017/0168039 A1 | 6/2017 | Lindsay et al. |
| 2017/0276678 A1 | 9/2017 | Ervin |
| 2018/0031549 A1 | 2/2018 | Chen et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0155773 A1 | 6/2018 | Gunderson et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0317040 A1 | 10/2019 | Lindsay et al. |
| 2019/0330695 A1 | 10/2019 | Guo et al. |
| 2019/0376135 A1 | 12/2019 | Mandell et al. |
| 2020/0157595 A1 | 5/2020 | Merriman et al. |
| 2021/0114025 A1 | 4/2021 | De Freitas Dias et al. |
| 2021/0208127 A1 | 7/2021 | Lindsay et al. |
| 2022/0252542 A1 | 8/2022 | Merriman et al. |

FOREIGN PATENT DOCUMENTS

| | | |
|---|---|---|
| WO | WO 2013/038272 | 3/2013 |
| WO | WO 2013/154999 | 10/2013 |
| WO | WO 2014/074727 | 5/2014 |
| WO | WO 2015/130781 | 9/2015 |
| WO | WO 2015/131073 | 9/2015 |
| WO | WO 2015/161119 | 10/2015 |
| WO | WO 2015/170784 | 11/2015 |
| WO | WO 2016/100635 | 6/2016 |
| WO | WO 2016/161402 | 10/2016 |
| WO | WO 2016/210386 | 12/2016 |
| WO | WO 2017/084998 | 5/2017 |
| WO | WO 2017/123416 | 7/2017 |
| WO | WO 2017/189930 | 11/2017 |
| WO | WO 2018/026855 | 2/2018 |
| WO | WO 2018/132457 | 7/2018 |
| WO | WO 2018/200687 | 11/2018 |
| WO | WO 2018/208505 | 11/2018 |
| WO | WO 2019/046589 | 3/2019 |
| WO | WO 2019/086305 | 5/2019 |
| WO | WO 2019/211622 | 11/2019 |
| WO | WO 2019/217600 | 11/2019 |
| WO | WO 2019/222527 | 11/2019 |
| WO | WO 2020/160300 | 8/2020 |
| WO | WO 2020/243207 | 12/2020 |
| WO | WO 2020/257654 | 12/2020 |
| WO | WO 2021/163275 | 8/2021 |
| WO | WO 2021/173681 | 9/2021 |
| WO | WO 2021/222791 | 11/2021 |

OTHER PUBLICATIONS

Main et al., Design of stable alpha-helical arrays from an idealized TPR motif. Structure. May 2003;11(5):497-508.

Mejias et al., Controlled nanometric fibers of self-assembled designed protein scaffolds. Nanoscale. Oct. 7, 2014;6(19):10982-8.

Sek et al., Conductance of alpha-helical peptides trapped within molecular junctions. J Phys Chem B. Oct. 5, 2006;110(39):19671-7.

Zhang et al., Role of contacts in long-range protein conductance. Proc Natl Acad Sci U S A. Mar. 26, 2019;116(13):5886-5891.

Zhang et al., Observation of Giant Conductance Fluctuations in a Protein. Nano Futures. 2017;1(3):035002. 25 pages.

International Search Report and Written Opinion for PCT/US21/34698. Mailed Sep. 30, 2021. 10 pages.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Kyte et al., A simple method for displaying the hydropathic character of a protein. J Mol Biol. May 5, 1982;157(1):105-32.

Pearson. Using the FASTA program to search protein and DNA sequence databases. Methods Mol Biol. 1994;24:307-31.

Zhang et al., Engineering an Enzyme for Direct Electrical Monitoring of Activity. ACS Nano. Feb. 25, 2020;14(2):1360-1368.

Zhang et al., Electronic Conductance Resonance in Non-Redox-Active Proteins. J Am Chem Soc. Apr. 1, 2020;142(13):6432-6438.

Zhang et al., Electronic Decay Length in a Protein Molecule. Nano Lett. Jun. 12, 2019;19(6):4017-4022.

Ackerman et al., Massively multiplexed nucleic acid detection with Cas13. Nature. Jun. 2020;582(7811):277-282.

Adhikari et al., Conductivity of individual Geobacter pili. RSC Advances, 2016. 6: p. 8354-8357.

Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.

(56) References Cited

OTHER PUBLICATIONS

Amdursky et al., Electronic transport via proteins. Adv Mater. Nov. 12, 2014;26(42):7142-61.
Amdursky et al., Solid-state electron transport via cytochrome c depends on electronic coupling to electrodes and across the protein. PNAS, Apr. 15, 2014, vol. 111, No. 15, pp. 5556-5561.
Anzai et al., Avidin-biotin complexation for enzyme sensor Applications, Trends in Analytical Chemistry, 1994, 13(5): 205-210.
Artes et al., Transistor-like Behavior of Single Metalloprotein Junctions. Nano Lett.,2012, 12(6), pp. 2679-2684 (publication date (Web): Oct. 5, 2011).
Aubert et al., Intraprotein radical transfer during photoactivation of DNA photolyase. Nature. Jun. 1, 2000;405(6786):586-90.
Ausubel et al. Current Protocols in Molecular Biology, John Wiley & Sons, New York, 1998. 19 pages.
Barhoumi et al., Urease immobilization on biotinylated polypyrrole coated ChemFEC devices for urea biosensor development, IRBM, Apr. 1, 2008, 29(2-3): 192-201.
Bayer et al., 3-(N-Maleimido-propionyl) Biocytin: A Versatile Thiol-Specific Biotinylating Reagent, Analytical Biochemistry, 1985, 149: 529-536.
Bostick et al., Protein bioelectronics: a review of what we do and do not know. Rep Prog Phys. Feb. 2018;81(2):026601. 58 pages.
Carter et al., Functional protein materials: beyond elastomeric and structural proteins, Polym. Chem. 2019, 10:2952-2959.
Castellarnau et al., Integrated microanalytical system based on electrochemical detection and cell positioning, Materials Science and Engineering, 2006, 26: 405-410.
Chang et al., Chemical recognition and binding kinetics in a functionalized tunnel junction. Nanotechnology. Jun. 15, 2012;23(23):235101. 28 pages.
Chen et al., DNA sequencing using electrical conductance measurements of a DNA polymerase, Nature Nanotechnology, May 5, 2013, pp. 1-7; https://doi.org/10.1038/nnano.2013.71. 7 pages.
Chichil et al., Linkers in the structural biology of protein-protein interactions. Protein Sci. Feb. 2013;22(2):153-67.
Chin et al., Addition of p-Azido-I-phenylalanine to the Genetic Code of *Escherichia coli*. J. Am. Chem. Soc. 2002. 124,31, 9026-9027.
Choi et al. Site-specific inhibition of integrin alpha v beta 3-vitronectin association by a serasp-val sequence through an Arg-Gly-Asp-binding site of the integrin, Proteomics, vol. 10, Issue 1, No. 1 Jan. 2010, pp. 72-80 (First published Oct. 30, 2009).
Choi et al., Single-Molecule Lysozyme Dynamics Monitored by an Electronic Circuit, Science (2012) 335:319-324.
Cui et al., Layer-by-layer 1 assembly of multilayer filme composed of avidin and biotin-labeled antibody for immunosensing, Biosensors And Bioelectronics, Jan. 1, 2003, 18(1): 59-67.
Cui et al., Reproducible measurement of single-molecule conductivity. Science. Oct. 19, 2001;294(5542):571-4.
Dellafiore et al., Modified Nucleoside Triphosphates for In-vitro Selection Techniques. Front Chem. May 4, 2016;4:18.
Dissertation by Joshua Sadar, Top-Down and Bottom-Up Strategies to Prepare Nanogap Sensors for Controlling and Characterizing Single Biomolecules, Jul. 2019, 160 pages.
Duffy et al., Modified nucleic acids: replication, evolution, and next-generation therapeutics. BMC Biology, Sep. 2, 2020. 18:112. 14 pages.
Fairhead et al., Plug-and-play pairing via defined divalent streptavidins. J Mol Biol. Jan. 9, 2014;426(1):199-214.
Fujino et al, Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Fulton et al., Purification of monoclonal antibody against Ebola GP1 protein expressed in Nicotiana benthamiana. J Chromatogr A. Apr. 10, 2015;1389:128-32.
Garg et al., Interface Electrostatics Dictates the Electron Transport via Bioelectronic Junctions. ACS Appl Mater Interfaces. Dec. 5, 2018;10(48):41599-41607.
Gerrits et al., Cell-Free Synthesis of Defined Protein Conjugates by Sitedirected Cotranslational Labeling, NCBI Bookshelf. Jan. 1, 2013, Retrieved from the Internet: URL:https://ww.ncbi.nlm.nih.gov/books/NBK6497.
Giese et al., Direct observation of hole transfer through DNA by hopping between adenine bases and by tunnelling. Nature. Jul. 19, 2001;412(6844):318-20.
Giese et al., Long distance charge transport through DNA: quantification and extension of the hopping model. Chemphyschem. Dec. 15, 2000;1(4):195-8.
Gonnet et al., Exhaustive matching of the entire protein sequence database. Science. Jun. 5, 1992;256(5062):1443-5.
Guo et al., Tuning electronic transport via hepta-alanine peptides junction by tryptophan doping. Proc Natl Acad Sci U S A. Sep. 27, 2016;113(39):10785-90.
Hajian et al., Detection of unamplified target genes via CRISPR-Cas9 immobilized on a graphene field-effect transistor. Nat Biomed Eng. Jun. 2019;3(6):427-437.
Harriman. Further comments on the redox potentials of tryptophan and tyrosine. Journal of Physical Chemistry 1987. 91:6102-6104.
Hays et al., Development of capacitance based immunosensors on mixed self-assembled monolayers. Sensors and Actuators B: Chemical, Apr. 26, 2006, 114(2): 1064-1070.
Hohl et al. Engineering a Polyspecific Pyrrolysyl-tRNA Synthetase by a High Throughput FACS Screen. Sci Rep. Aug. 19, 2019;9(1):11971.
Hozel et al., Trapping Single Molecules by Dielectrophoresis, Physical Review Letters, 2005, 128102-1-4.
Ihalainene et al., Application of paper-supported printed gold eletrodes for impedimetric immunosensor development, Biosensors 2013, 3:1-17.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kotlowski, Fine discrimination of volatile compounds by graphene-immobilized odorant-binding proteins, Sensors and Actuatores B: Chemical 2018 (256): 564-72.
Krishnan et al., Long-Range Conductivity in Proteins Mediated by Aromatic Residues, ACS Phys. Chem Au 2023, 3:444-455.
Lagunas et al., Long distance electron transfer through the aqueous solution between redox partner proteins. Nat Commun. Dec. 4, 2018;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminiviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., CRISPR-SE: a brute force search engine for CRISPR design. NAR Genom Bioinform. Feb. 23, 2021;3(1):lqab013.
Lindsay et al., Recognition tunneling, Nanotechnology 2010, 21:262001, 12 pp.
Liu et al., Vertical T cellimmunodomincance and epitope entropy determine HIV-1 escape. J Clin Invest. Jan. 2013; 123(1):380-93.
Maalouf R. et al., Label-Free Detection of Bacteria by Electrochemical Impedance Spectroscopy: Comparison to Surface Plasmon Resonance. Anal. Chem, May 25, 2007, vol. 79, No. 13, pp. 4879-4886.
Malvankar et al., Tunable metallic-like conductivity in microbial nanowire networks. Nat Nanotechnol. Aug. 7, 2011;6(9):573-9.
Marakova et al., An updated evolutionary classification of CRISPR-Cas systems. Nat Rev Microbiol. Nov. 2015;13(11):722-36.
Mckenzie et al., Recent progress in non-native nucleic acid modifications. Chem Soc Rev. Apr. 26, 2021;50(8):5126-5164.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Nitzan. Chemical dynamics in condensed phases. Oxford University Press., Oxford. 2006. TOC only. 13 pages.

(56) References Cited

OTHER PUBLICATIONS

Odella et al., Controlling Proton-Coupled Electron Transfer in Bioinspired Artificial Photosynthetic Relays. J Am Chem Soc. Nov. 14, 2018;140(45):15450-15460.

Olsen et al., Electronic Measurements of Single-Molecule Processing by DNA Polymerase I (Klenow Fragment), Journal of the American Chemical Society (Apr. 30, 2013); pp. 1-12; DOI: 10.1021/ja311603r.

Ouerghi et al., Impedimetric immunosensor using avidin-biotin for antibody immobilization, Bioelectrochemistry, May 15, 2002, 56(1-2): 131-133.

Pang et al. Fixed-Gap Tunnel Junction for Reading DNA Nucleotides, ACS Nano, 2014, 8(12), pp. 11994-12003 (Publication Date (Web): Nov. 7, 2014).

Prodromidis et al., Impedimetric immunosensors—A review, Electrochimica Acta, May 30, 2010, 55(14): 4227-4233.

Quast et al., Cotranslational incorporation of non-standard amino acids using cell-free protein synthesis. FEBS Lett. Jul. 8, 2015;589(15):1703-12.

Ruiz et al., Bioengineering a Single-Protein Junction. J Am Chem Soc. Nov. 1, 2017;139(43):15337-15346.

Sambrook et al., Molecular Cloning: A Laboratory Manual, 3d ed., Cold Spring Harbor Press, 2001. TOC only. 23 pages.

Sano et al., Cooperative biotin binding by streptavidin. Electrophoretic behavior and subunit association of streptavidin in the presence of 6 M urea. J Biol Chem. Feb. 25, 1990;265(6):3369-73.

Seifert, Characterization of Streptavidin Binding to Biotinylated, Binary Self-Assembled Thio Monolayers—Influence of Component Ratio and Solvent, Langmuir, 2010, 26(9): 6386-93.

Sela-Culang et al., The strutural basis of antibody-antigen recognition, Frontiers in Immunology, 2013, vol. 4, 13 pages.

Sequences of amino acids as found on the world wide web at bmrb.wisc.edu/referenc/choufas. 4 pages.

Shimura & Yoshida, Heterogeneous photocatalytic hydrogen production from water and biomass derivatives, Energy Environmental Science 2011, 4: 2467.

Smith. The hydrophilic nature of a clean gold surface. J. Colloid Interface Science 1980. 75:51-55.

Staals et al., RNA targeting by the type III-A CRISPR-Cas Csm complex of Thermus thermophilus. Mol Cell. Nov. 20, 2014;56(4):518-30.

Tripkovic et al., Standard hydrogen electrode and potential of zero charge in density functional calculations. Phys. Rev. B 2011. 84:115452.

Tuchband et al., Insulated gold scanning tunneling microscopy probes for recognition tunneling in an aqueous environment. Rev Sci Instrum. Jan. 2012;83(1):015102.

Uygun et al., CRISPR-dCAS9 powered impedimetric biosensor for label-free detection of circulating tumor DNAs, Analytica Chimica Acta 2020, 1121:35-41.

Vaish et al., A novel, modification-dependent ATP-binding aptamer selected from an RNA library incorporating a cationic functionality. Biochemistry. Jul. 29, 2003;42(29):8842-51.

Varga et al., Binding of a Mouse Monoclonal IgE (anti-DNP) antibody to radio-derivatized polystyrene-DNP complexes, The FASEB Journal, Federation of American Societies for Experimental Biology, Jun. 1, 1990, 4(9): 2678-2683.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018; 16(2):572-580.

Yoon, Hidden Markov Models and their Applications in Biological Sequence Analysis, Current Genomics, 2009, 10:402-415.

Zhang et al., Electronic Transport in Molecular Wires of Precisely Controlled Length Built from Modular Proteins, ACS Nano 2022, 16(1): 1671-1680.

Zwolak et al. Electronic Signature of DNA Nucleotides via Transverse Transport, NanoLett., 2005, 5(3), pp. 421-424 (Publication Date (Web): Feb. 12, 2005).

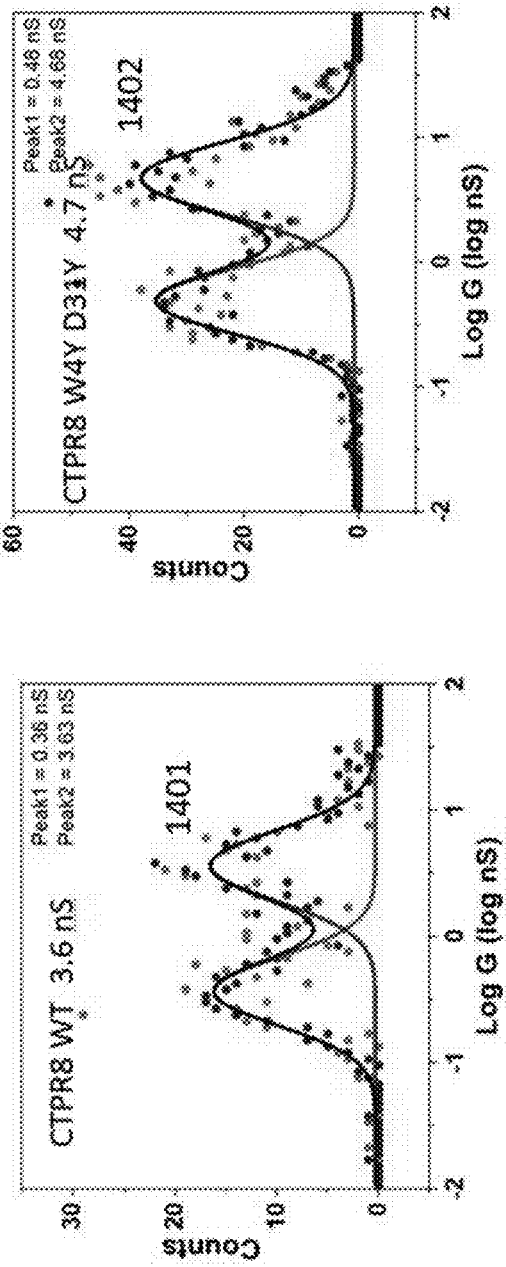

BIOELECTRONIC DEVICES WITH PROGRAMMABLE ADAPTORS

RELATED APPLICATIONS

This application claims priority to and the benefit of U.S. Provisional Patent Application No. 63/032,266 filed May 29, 2020, and U.S. Provisional Patent Application No. 63/125,674 filed Dec. 15, 2020, both of which are incorporated herein by reference in their entireties for all purposes.

GOVERNMENT SUPPORT

This invention was made with government support under R21 HG010522 awarded by the National Institutes of Health. The government has certain rights in the invention.

FIELD

The present disclosure provides devices, systems, and methods related to bioelectronic devices. In particular, the present disclosure provides bioelectronic devices, and methods of making bioelectronic devices, comprising adjustable adaptor polypeptides with repeatable motifs and enhanced conductive properties. The bioelectronic devices and methods of the present disclosure are useful for a variety of applications, including the direct measurement of protein activity (e.g., when sequencing a biopolymer).

BACKGROUND

Proteins make excellent electronic conductors when contacted by strong chemical bonds. In some cases, they transport current with less resistance per unit distance than is the case for conventional molecular wires for distances in excess of, for example, 5 nm. One important aspect of this property is folding into a structure that has a hydrophobic core surrounded by a hydrophilic exterior. Accordingly, isolated peptides can be insulators. Previous teachings have utilized an alpha helix as a connecting arm to wire an enzyme into a circuit. However, isolated peptide sequences do not conduct, as shown by break junction measurements on small peptides. For example, peptide sequences examined in break junctions include peptides that fold into alpha helices, and these exhibit a rapid decay of current with distance on the order of a tenfold decrease for each half nanometer of distance. Thus, they function as insulators and cannot be used as molecular wires. Therefore, the need exists for bioelectronic devices, and methods of building such devices, that include functional protein molecular wires (e.g., a fully-folded polypeptide with a hydrophobic core surrounded by a hydrophilic exterior) that can conform to a range of lengths within the bioelectronic device and can be precisely controlled with any desired functionalization.

SUMMARY

Embodiments of the present disclosure include a bioelectronic device comprising a first electrode and a second electrode separated by a gap, a protein attached to the first and second electrodes via a linker, and at least one adaptor polypeptide coupled to the protein, thereby stabilizing the protein within the gap.

In some embodiments, the at least one adaptor polypeptide comprises two adaptor polypeptides, each adaptor polypeptide coupled to the protein at difference positions on the protein.

In some embodiments, the at least one adaptor polypeptide comprises a hydrophobic core. In some embodiments, the at least one adaptor polypeptide comprises a hydrophilic exterior. In some embodiments, the at least one adaptor polypeptide is capable of folding into a stable conformation.

In some embodiments, the at least one adaptor polypeptide comprises at least one repeatable motif. In some embodiments, the number of repeatable motifs is adjustable based on the size of the gap between the first and second electrodes. In some embodiments, the at least one repeatable motif comprises an α-helix and/or a β-sheet. In some embodiments, the at least one repeatable motif comprises at least two α-helices. In some embodiments, the at least one repeatable motif comprises a β-barrel.

In some embodiments, the at least one adaptor polypeptide comprises at least one aromatic amino acid positioned within its hydrophobic core. In some embodiments, the at least one adaptor polypeptide comprises at least one amino acid substitution from a non-aromatic amino acid to an aromatic amino acid positioned within its hydrophobic core. In some embodiments, the at least one aromatic amino acid is tyrosine, tryptophan, or phenylalanine.

In some embodiments, the at least one adaptor polypeptide comprises a C-terminal and/or N-terminal cysteine residue.

In some embodiments, the at least one adaptor polypeptide is directly coupled to at least one of the first and second electrodes.

In some embodiments, the at least one adaptor polypeptide is coupled to at least one of the first and second electrodes via a linker. In some embodiments, the linker is selected from the group consisting of a biotin-streptavidin linker, a spytag-spycatcher linker, a halotag linker, a thiolated linker, a thiolated TPR linker, and a thiolated CTPR linker.

In some embodiments, the at least one adaptor polypeptide is directly coupled to the protein.

In some embodiments, the at least one adaptor polypeptide is coupled to the protein electrodes via a linker. In some embodiments, the linker is selected from the group consisting of a biotin-streptavidin linker, a spytag-spycatcher linker, a halotag linker, a thiolated linker, a thiolated TPR linker, and a thiolated CTPR linker.

In some embodiments, the at least one adaptor polypeptide comprises a consensus tetratricopeptide repeat (CTPR) adaptor polypeptide. In some embodiments, the CTPR is selected from the group consisting of CTPR1, CTPR2, CTPR3, CTPR4, CTPR5, CTPR6, CTPR7, CTPR8, CTPR9, CTPR10, CTPR11, CTPR12, CTPR13, CTPR14, CTPR15, CTPR16, CTPR17, CTPR18, CTPR19, CTPR20, and any derivatives or variants thereof.

In some embodiments, the device comprises two CTPR adaptor polypeptides, and the two CTPR adaptor polypeptides are the same size. In some embodiments, the device comprises two CTPR adaptor polypeptides, and each CTPR adaptor polypeptide is a different size.

In some embodiments, the presence of the adaptor polypeptide reduces conductance decay as the gap between the first and second electrodes increases.

In some embodiments, the protein is selected from the group consisting of a polymerase, a nuclease, a proteasome, a glycopeptidase, a glycosidase, a kinase and an endonuclease.

In some embodiments, the linker and/or the at least one adaptor polypeptide is coupled to an inactive region of the protein.

In some embodiments, the protein and the first and second electrodes are biotinylated, and the linker comprises a streptavidin molecule comprising at least two biotin binding sites.

In some embodiments, the linker comprises a distinctive negative charge. In some embodiments, the distinctive negative charge is conferred by addition of a glutamate moiety, an aspartate moiety, or a combination thereof, coupled to the linker. In some embodiments, the distinctive negative charge increases conductance through the protein.

In some embodiments, the linker comprises a distinctive positive charge. In some embodiments, the distinctive positive charge is conferred by addition of an arginine moiety, a histidine moiety, a lysine moiety, or a combination thereof, coupled to the linker. In some embodiments, the distinctive positive charge increases or decreases conductance through the protein.

In some embodiments, the first and/or the second electrode comprises gold, palladium, platinum, silver, copper, or any alloys thereof.

In some embodiments, the device comprises a dielectric layer at least partially covering a surface of the first and/or second electrode.

In some embodiments, the first electrode and second electrode are positioned so that about a 1 nm to about a 50 nm gap is formed between the two electrodes.

Embodiments of the present disclosure also include a system comprising a plurality of the devices described herein.

Embodiments of the present disclosure also include a method of measuring electronic conductance through a protein using any of the devices described herein.

Embodiments of the present disclosure also include a method for direct electrical measurement of protein activity. In accordance with these embodiments, the method includes introducing an analyte capable of interacting with the protein to any of the bioelectronic devices described herein, applying a voltage bias between the first and second electrodes that is 100 mV or less, and observing fluctuations in current between the first and second electrodes that occur when the analyte interacts with the protein.

In some embodiments, the analyte is a biopolymer selected from the group consisting of a DNA molecule, an RNA molecule, a peptide, a polypeptide, and a glycan.

BRIEF DESCRIPTION OF THE DRAWINGS

FIGS. 20A-20D: Representative graphs of the distributions of conductances measured for wildtype (C) and a W4Y/D31Y mutant (D) showing a significant increase in conductance when the tyrosine content is increased, according to one embodiment of the present disclosure. The sequence of the helix-turn-helix motif for the wild-type (WT) is shown in (A), and the sequence of the W4Y D31Y mutant is shown in (B). Tyrosines marked in yellow with the additional tyrosines pointed to by blue arrows.

DETAILED DESCRIPTION

Figure 1:
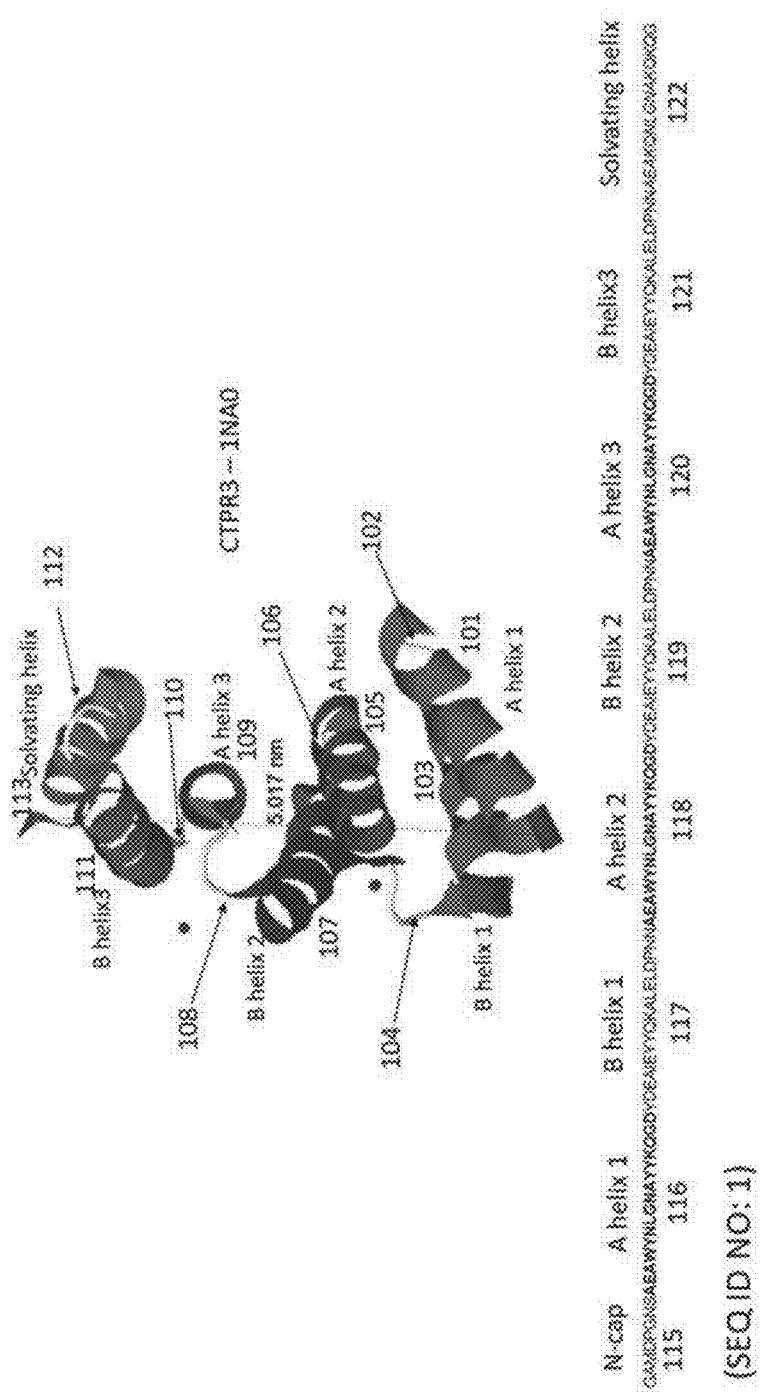
FIG. 1: Representative diagram of the structure of a consensus tetratricopeptide repeat (CTPR) protein (SEQ ID NO. 1), according to one embodiment of the present disclosure.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

Unless otherwise noted, technical terms are used according to conventional usage. Definitions of common terms in molecular biology can be found in Benjamin Lewin, *Genes IX*, published by Jones and Bartlet, 2008 (ISBN 0763752223); Kendrew et al. (eds.), *The Encyclopedia of Molecular Biology*, published by Blackwell Science Ltd., 1994 (ISBN 0632021829); and Robert A. Meyers (ed.), *Molecular Biology and Biotechnology: a Comprehensive Desk Reference*, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

Section headings as used in this section and the entire disclosure herein are merely for organizational purposes and are not intended to be limiting.

1. Definitions

To facilitate review of the various embodiments of the disclosure, the following explanations of specific terms are provided below. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, "biological sample" generally refers to a biological specimen containing genomic DNA, RNA (such as mRNA), protein, or combinations thereof, obtained from a subject. Examples include, but are not limited to, saliva, peripheral blood, urine, tissue biopsy, surgical specimen, and autopsy material. In embodiments, the biological sample is a bodily fluid, such as blood, or a component thereof, such as plasma or serum.

As used herein, "biopolymer" generally refers to polymers (e.g., produced by living organisms or synthetically generated). Biopolymers contain monomeric units that are covalently bonded to form larger structures. There are three main classes of biopolymers, classified according to the monomeric units used and the structure of the biopolymer formed: polynucleotides (RNA and DNA), which are long polymers composed of 13 or more nucleotide monomers; polypeptides, which are short polymers of amino acids; and polysaccharides, which are often linear bonded polymeric carbohydrate structures. Other examples of biopolymers include rubber, suberin, melanin and lignin.

As used herein, an "isolated" biological component (e.g., such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

As used herein, "modification," "chemical modification," or "chemically modified" generally refers to any of a number of various processes involving the alteration of the chemical constituent or structure of molecules. For example, a polymerase can be chemically modified to form a chemical bond with a first electrode and a second electrode. In one example, a chemically-modified electrode is an electrode that has a surface chemically converted to change the electrode's properties, such as its physical, chemical, electrochemical, optical, electrical, and/or transport characteristics. As provided herein, the chemical modification can also involve chemically altering a polymerase so that it is compatible with a linker that binds to an electrode (e.g., SypCatcher/SpyTag, biotin/streptavidin, HaloTag, and the like). In other embodiments, a modification can be generated via protein synthesis. For example, a polymerase can be designed to comprise one or more modifications (e.g., a linker) when synthesized from a polynucleotide that encodes the protein and the modification (e.g. linker).

As used herein, "contact" and "contacting" can include placement in direct physical association, including both a solid and liquid form. "Contacting" can include a specific chemical contact between two different substances (e.g., covalent bond, or non-covalent bond having specific ligand interaction with specific amino acid residues).

As used herein, "complementarity" or "complementary" generally refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" generally indicates that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "current stream" generally refers to a current signal generated over time, such as from the bio-electronic devices of the present disclosure.

As used herein, a "label" generally refers to an agent capable of detection, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

As used herein, the term "linker" or "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). In several embodiments, linked components are associated in a chemical or physical manner so that the components are not freely dispersible from one another. For example, two components may be covalently bound to one another so that the two components are incapable of separately dispersing or diffusing. In several embodiments, linked components are associated in a chemical or physical manner so that the components are not freely dispersible from one another. For example, two components may be covalently bound to one another so that the two components are incapable of separately dispersing or diffusing.

As used herein, the terms "non-naturally occurring" and "engineered" interchangeably indicate the involvement of the hand of man. These terms, when referring to nucleic acid molecules or polypeptides, generally indicate that the nucleic acid molecule or the polypeptide is at least substantially free from at least one other component with which they are naturally associated in nature and as found in nature.

As used herein, "nucleic acid" generally refers to a deoxyribonucleotide or ribonucleotide polymer, which can include analogues of natural nucleotides that hybridize to nucleic acid molecules in a manner similar to naturally occurring nucleotides. In one example, a nucleic acid molecule is a single stranded (ss) DNA or RNA molecule, such as a probe or primer. In another example, a nucleic acid molecule is a double stranded (ds) nucleic acid. In another example, a nucleic acid is a modified DNA or RNA molecule, such as a xenonucleic acid (XNA). The term "nucleotide" generally refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

As used herein, "polypeptide," "peptide," and "protein" generally refer to a polymer in which the monomers are amino acid residues that are joined together through amide bonds. When the amino acids are alpha-amino acids, either the L-optical isomer or the D-optical isomer can be used, the L-isomers being preferred in nature. The term polypeptide is specifically intended to cover naturally occurring proteins, as well as those that are recombinantly or synthetically produced. A substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl. Variant amino acid sequences may, for example, be 80, 90 or even 95 or 98% identical to the native amino acid sequence. Programs and algorithms for determining percentage identity can be found at the NCBI website.

As used herein, "probe" generally refers to a short sequence of nucleotides, such as at least 8, at least 10, at least 15, at least 20, or at least 21 nucleotides in length, which can be used to detect the presence of a complementary sequence by molecular hybridization. In particular examples, oligonucleotide probes include a label that permits detection of oligonucleotide probe:target sequence hybridization complexes. Laboratory standards and values can be set based on a known or determined population value and can be supplied in the format of a graph or table that permits comparison of measured, experimentally determined values.

As used herein, "primer" generally refers to a short nucleic acid molecule, for instance DNA oligonucleotides 10-100 nucleotides in length, such as 5, 6, 7, 8, 9, 10, 11, 12, or more in length. Primers can be annealed to a complementary target nucleic acid strand by nucleic acid hybridization to form a hybrid between the primer and the target nucleic acid strand. Primers can be used for amplification of a nucleic acid sequence, such as by PCR or other nucleic acid amplification methods known in the art.

As used herein, the term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is purer than in an environment including a complex mixture of oligonucleotides. Purity of a compound may be determined, for example, by high performance liquid chromatography (HPLC) or other conventional methods.

As used herein, "recombinant" generally refers to recombinant nucleic acid or protein that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

As used herein, the term "subject" includes human and non-human animals. "Patient" and "subject" are used interchangeably herein.

As used herein, the terms, "substantial identity" or "substantially identical" generally refer to a nucleic acid or fragment thereof, that, when optimally aligned with appropriate nucleotide insertions or deletions with another nucleic acid (or its complementary strand), refers to a nucleotide sequence having at least about 95% sequence identity, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, "variant" generally refers to a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e. replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "pause" generally refers to a section of a current stream in which the fluctuations in measured current are interrupted by a slower feature of about twice the duration of the neighboring features. Typically, a pause is observed before and after a nucleotide has been incorporated into a template sequence, and the duration of the pause relative to the neighboring pulses of current increases as the concentration of nucleotide triphosphates is lowered.

As used herein, a "polymerase" generally refers to an enzyme that synthesizes long chains of polymers or nucleic acids. DNA polymerase and RNA polymerase are used to assemble DNA and RNA molecules, respectively, by copying a DNA template strand using base-pairing interactions or RNA by half ladder replication.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As noted herein, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting protein activity. In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

2. Bioelectronic Devices and Systems

Embodiments of the present disclosure include devices, systems, and methods related to bioelectronic devices. In particular, the present disclosure provides bioelectronic devices, and methods of making bioelectronic devices, comprising adjustable adaptor polypeptides with repeatable motifs and enhanced conductive properties. The bioelectronic devices and methods of the present disclosure are useful for a variety of applications, including the direct measurement of protein activity (e.g., when sequencing a biopolymer).

In some embodiments, embodiments of the present disclosure include molecular wires comprising adaptor polypeptides having precisely controlled length and functionalization for use in bioelectronic circuits. As disclosed further herein, adaptor polypeptides can include any protein, polypeptide, or peptide that exhibits certain characteristics or properties suitable for use in a bioelectronic circuit. In embodiments, an adaptor polypeptide is a polypeptide or protein that folds into a stable conformation so as to exclude water from an interior region (e.g., comprises a hydrophilic exterior and a hydrophobic interior or core region). In some embodiments, the adaptor polypeptide comprises a first reactive group at a first location or position on the protein and a second reactive group at a second location or position on the protein. In some embodiments, a first reactive group is bonded to one element in an electronic circuit and a second reactive group is bonded to a second element in an electronic circuit such that current can pass between the first circuit element and the second circuit element via the protein. In some embodiments, the first and/or second reactive elements are conjugated to a linker that facilitates a connection between the protein to at least one element in an electronic circuit.

Figure 2:
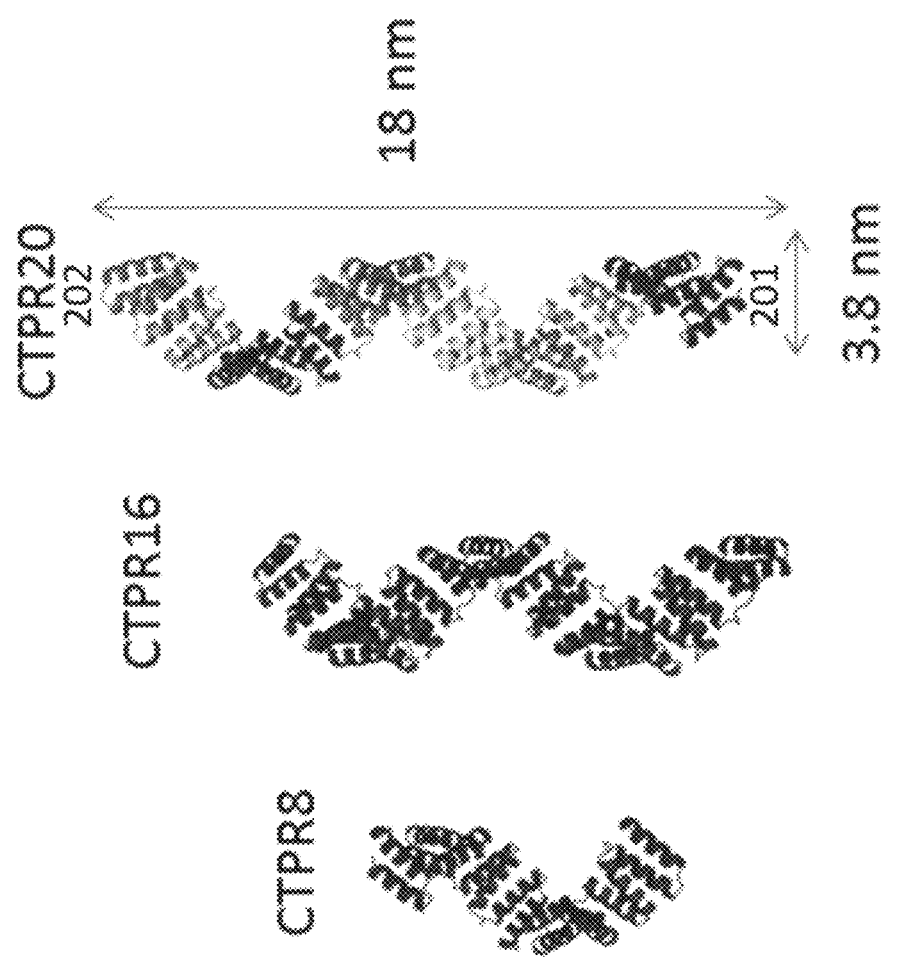
FIG. 2: Representative diagrams of the structures of three CTPR polypeptides (e.g., adaptor polypeptides) having different lengths, according to one embodiment of the present disclosure.
Figure 17:
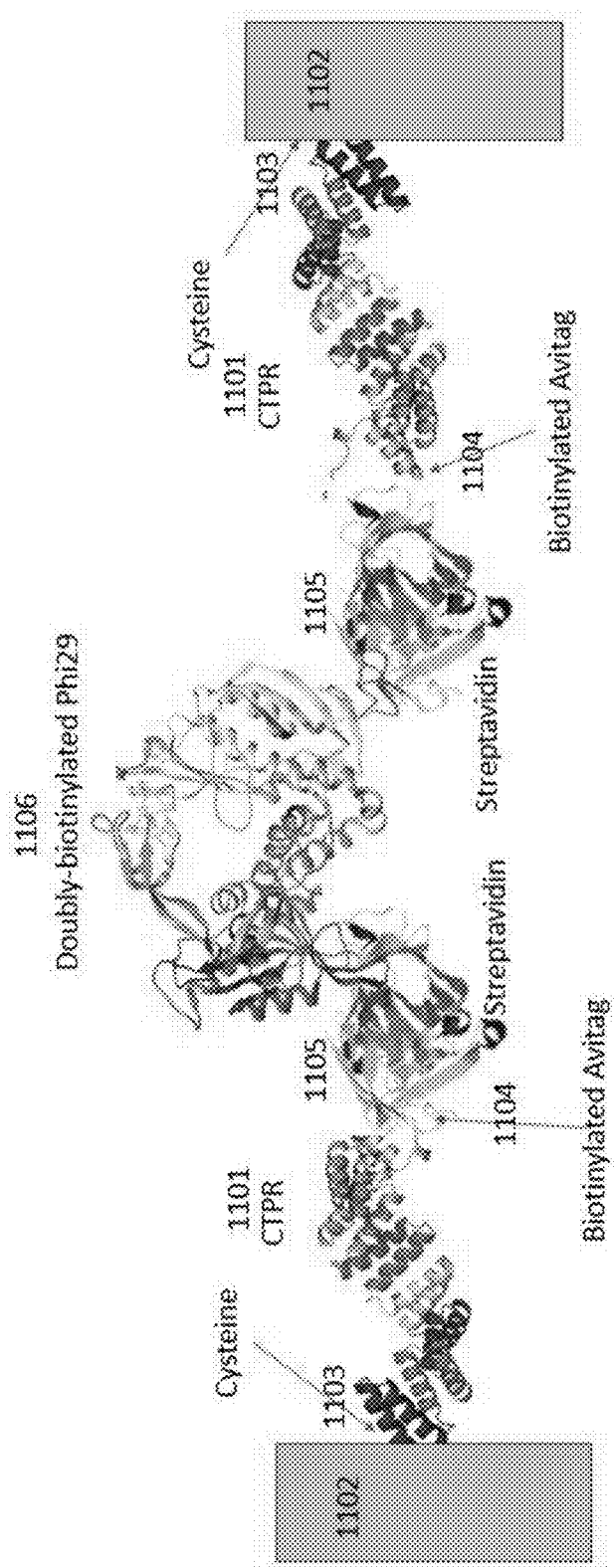
FIG. 17: Representative diagram of a self-assembled bioelectronic circuit in which CTPR molecular wires were used to span the gap size for measuring enzyme fluctuations, according to one embodiment of the present disclosure.

In embodiments, a protein-of-interest (e.g., a polymerase) that is to be positioned within a bioelectronic circuit (e.g., between two electrodes) is stabilized using an adaptor polypeptide or protein (see, e.g., FIG. 17). In some embodiments, the adaptor polypeptide has a long axis or is rod-shaped, with available attachment points separated by a distance that is similar to or equal to the longest dimension of the protein (see, e.g., FIG. 2). Such geometries are often realized in proteins that are comprised of bundles of two or more alpha helices and/or two or more β-sheets (e.g., repeatable protein motifs which allow the protein to be engineerable in length). Another such geometry can be provided using proteins comprising a β-barrel motif(s). Generally, the adaptor polypeptides or proteins are stable against changes in pH, salinity, and temperature, and can be readily expressed in a bacterium such as *E. Coli* by means well known in the art. In some embodiments, the adaptor polypeptides or proteins are less prone to proteolytic cleavage.

One exemplary adaptor polypeptide is the consensus tetratricopetide repeat (CTPR) protein. For example, CTPR3 is shown in FIG. 1, and has three repeatable motifs. The basic unit consists of an A helix 101 connected via a linker sequence 102. The linker allows the B helix 103 to fold back onto the A helix where it is held by hydrophobic interactions. In the case of the protein shown in FIG. 1 (CTPR3), this basic motif is repeated three times: linker 104 connecting to A helix 2 105, which is connected via linker 106 to B helix 2 107, completing the second repeat. The third repeat is formed by helices 109 and 111 together with linkers 108 and 110. The structure is connected via 112 to a solvating helix 113. In this exemplary structure, the N- and C-termini are separated by 5 nm allowing this structure to transport sufficient electrical charge over this distance.

The amino acid sequence of CTPR3 is shown at the bottom of FIG. 1 (GAMDPGNSAEAWYNLG-NAYYKQGDYDEAIEYYQKALELDPNNAEAWYNLG-NAY YKQGDYDEAIEYYQKALELDPNNAEAWYNLG-NAYYKQGDYDEAIEYYQKALELDP NNAEAKQNL-GNAKQKQG (SEQ ID NO: 1)). The N-terminal sequence 115 can include a HIS-tag if desired, for example, for purification of the final product. The sequence of A helix 1 is shown in bold type 110, followed by the sequence of B helix 1 117. A helix 2 and A helix 3 are 118 and 120, while B helix 2 and B helix 3 are 119 and 121. The solvating helix is represented as 122. Additionally, the N- and C-termini are readily available for incorporation of a reactive site, which includes but is not limited to, a cysteine residue (see, e.g., FIG. 8). In some embodiments, a non-canonical amino acid can be used, including but not limited to, an azido group for click chemistry reactions. In other embodiments, a reactive peptide sequence such as a SpyTag or an Avitag is incorporated (see, e.g., FIGS. 5, 6, and 17). In some embodiments, the entire SpyCatcher sequence can be included at both ends of an adaptor polypeptide or protein-of-interest. These and other configurations can comprise various linkers that are available and known in the art, including but not limited to, a biotin-streptavidin linker, a spytag-spycatcher linker, a halotag linker, a thiolated linker, a thiolated TPR linker, and a thiolated CTPR linker.

In some embodiments, the CTPR adaptor polypeptides are readily cloned and expressible as a series of polymers of any desirable length. In some embodiments, the CTPR adaptor polypeptides are readily cloned and expressible as a series of polymers up to and including CTPR20. In some embodiments, the CTPR adaptor polypeptides are readily cloned and expressible as a series of polymers of CTPR20 or greater. For example, in some embodiments, the CTPR adaptor polypeptide is CTPR1, CTPR2, CTPR3, CTPR4, CTPR5, CTPR6, CTPR7, CTPR8, CTPR9, CTPR10, CTPR11, CTPR12, CTPR13, CTPR14, CTPR15, CTPR16, CTPR17, CTPR18, CTPR19, or CTPR20, and any derivatives or variants thereof (see, e.g., FIG. 2). CTPR20, for example, when functionalized at the N- and C-termini (201 and 202 in FIG. 2, respectively) constitutes a molecular a wire capable of transporting charge over a distance of 18 nm.

Figure 3:
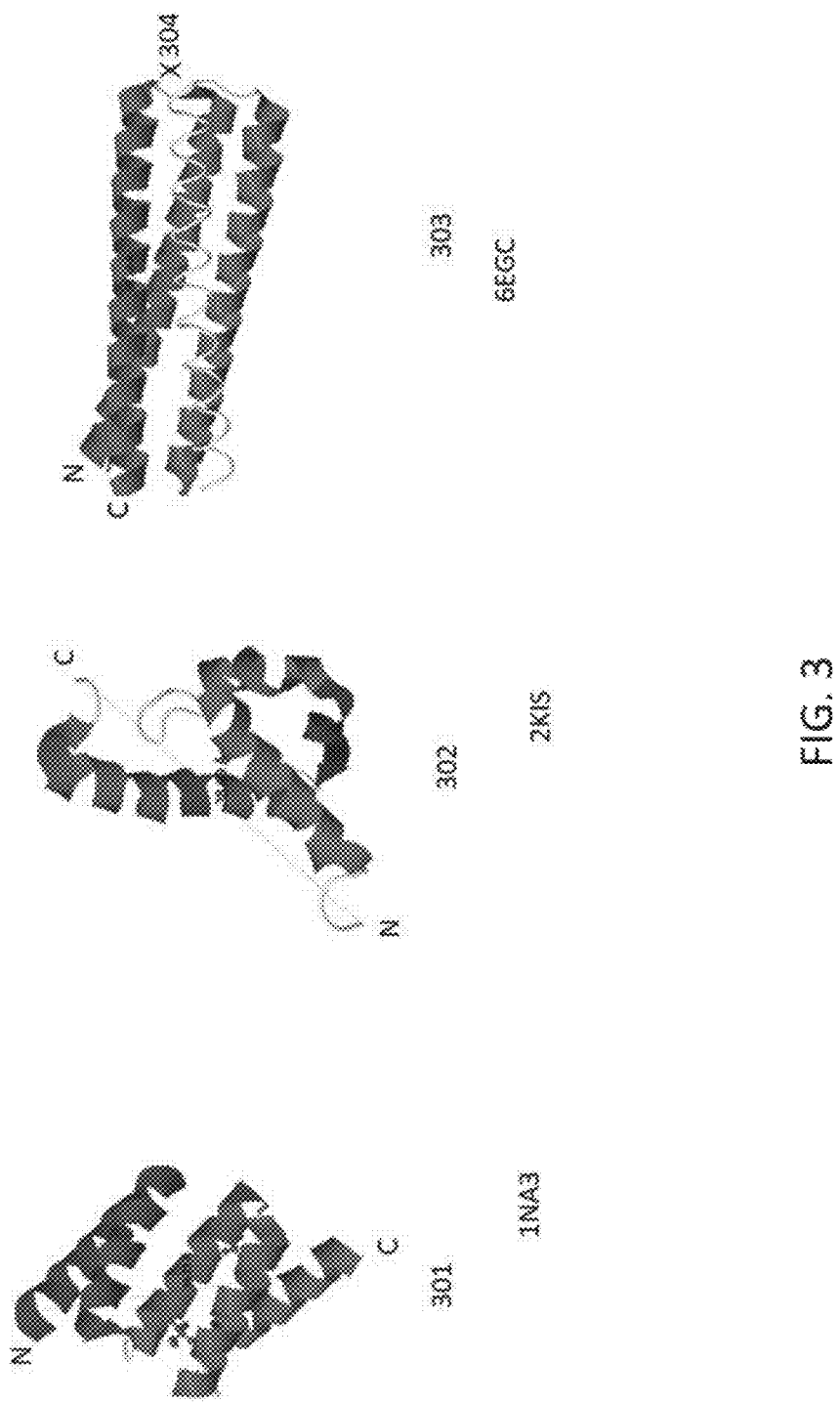
FIG. 3: Representative diagrams of the structures of three synthetic adaptor polypeptides comprising helix bundles, according to one embodiment of the present disclosure.

Many other helix-bundle proteins and polypeptides can serve as molecular wires, in addition to CTPR-based molecular wires. Examples of three synthetic helix bundle proteins are provided in FIG. 3. For example, in protein 301 (RSC PDB reference 1NA3), the N- and C-termini are separated by 3.9 nm. For protein 302 (RSC PDB reference 2KIS), the N- and C-termini are separated by 3.8 nm. And for protein 303 (RSC PDB reference 6EGC), the N- and C-termini are close together, but proteins with folds such as this can still be used as molecular wires by inserting a non-canonical amino acid with a reactive group (e.g., an azido group) in loop 304 (marked "X").

Figure 4:
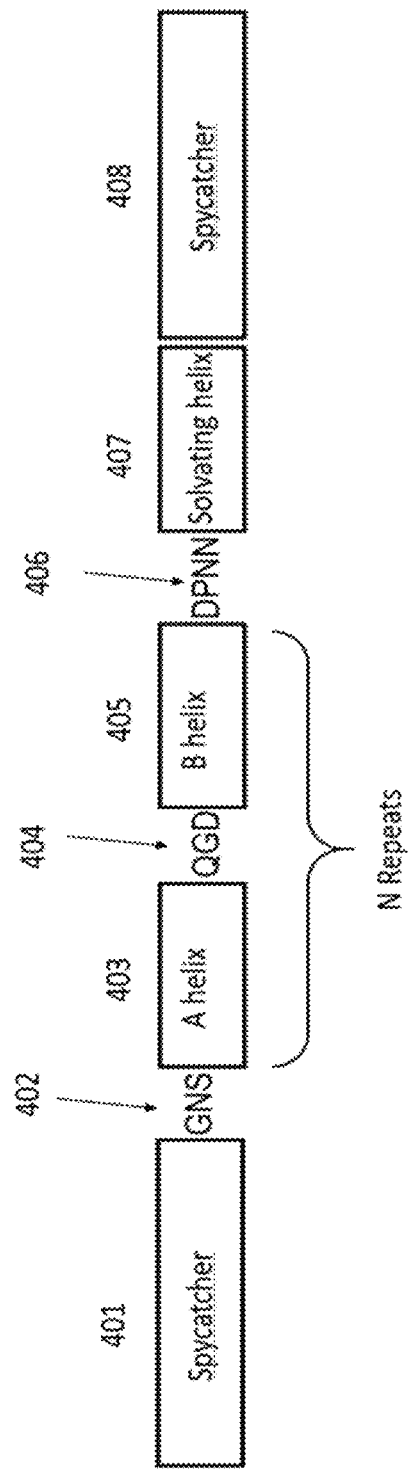
FIG. 4: Representative diagram of an adaptor polypeptide configuration comprising a CTPR polypeptide conjugated with SpyCatcher peptides at either end, according to one embodiment of the present disclosure.

One general approach for making functionalized molecular wires, as disclosed further herein, is to use a linker capable of attachment to an adaptor polypeptide. For example, a fusion protein capture construct can be used, which includes the gene for the linker, such as the gene for a SpyCatcher protein, at each end of the DNA sequence from which an adaptor polypeptide (e.g., CTPR protein) is expressed. The consequent protein sequence is illustrated in FIG. 4. The construct begins with the Spycatcher sequence 401, which includes a HIS-tag for protein purification. The helix capping sequence 402 connects to N repeats comprising an A helix 403 connected via the QGD linker 404 to a B helix 405. A linker 406 connects to the solvating helix and finally to a repeat of the SpyCatcher sequence 408.

Figure 5:
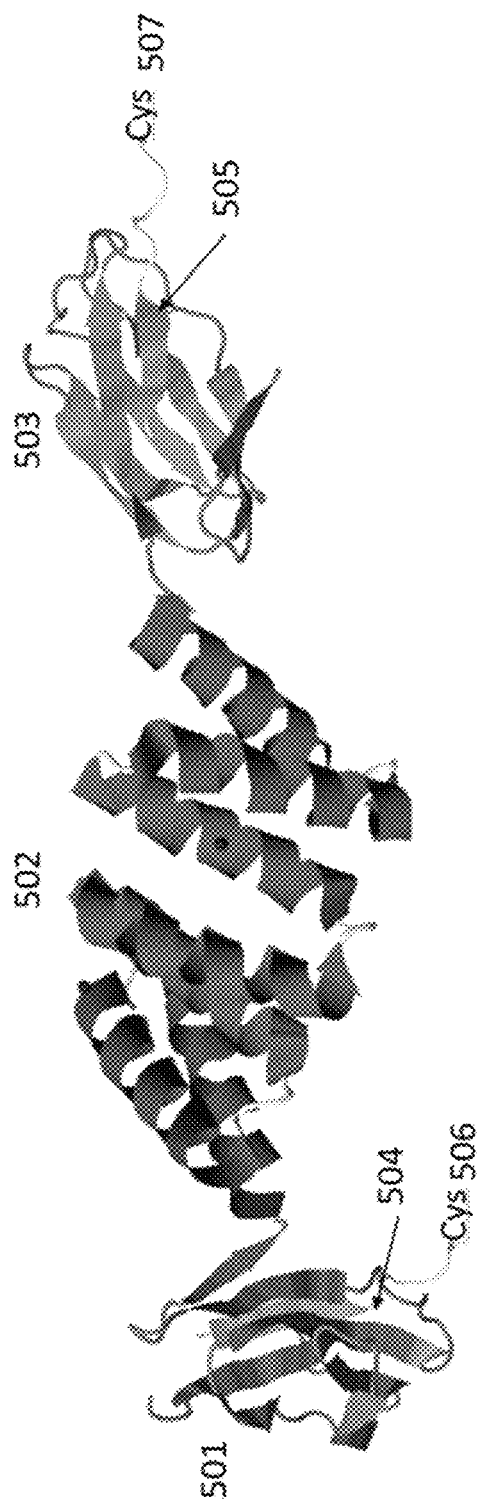
FIG. 5: Representative diagram of the structure of an adaptor polypeptide configuration comprising a SpyCatcher-terminated CTPR polypeptide with bonded SpyTags, according to one embodiment of the present disclosure.

The structure of such a complex with a CTPR3 protein is shown in FIG. 5. A first SpyCatcher protein 501 is concatenated to the CTPR3 protein 502 at its N-terminus. A second SpyCatcher 503 is concatenated to the C-terminus of the CTPR3 protein. Also shown are the SpyTags 504 and 505 that form isopeptide bonds with the SpyCatcher proteins. Terminated in a reactive group such as a cysteine 506, 507, SpyTags can be attached to electrodes or other proteins.

Figure 6:
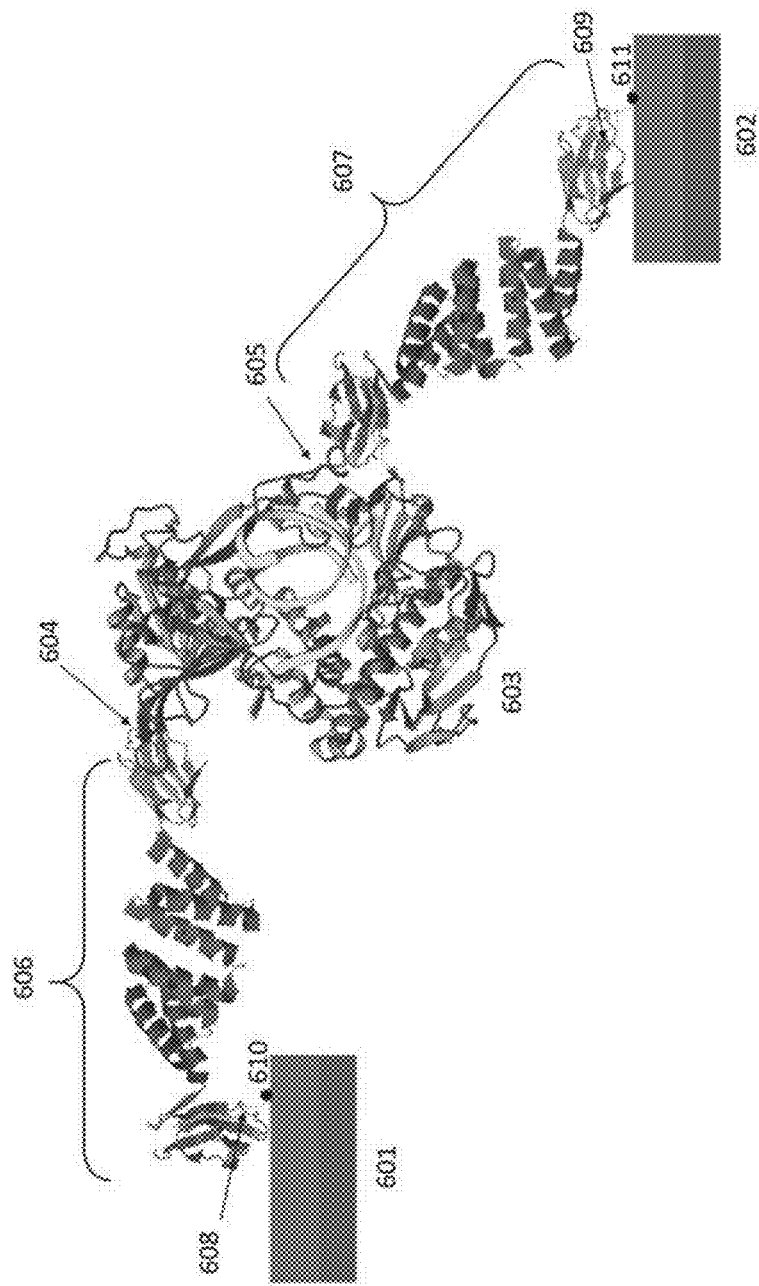
FIG. 6: Representative diagram of a polymerase Φ29 bridging a pair of electrodes by means of SpyCatcher-terminated CTPR polypeptide arms and SpyTag functionalized electrodes, according to one embodiment of the present disclosure.

An example of a bioelectronic circuit comprising CTRP adaptor polypeptides and SpyCatcher/SpyTag linkers is provided in FIG. 6. Here, two electrodes 601, 602 are connected together by a self-assembling complex. In this example, a polymerase 029 603 is functionalized with a SpyTag sequence (SEQ ID NO: 2, AHIVMVDAYKPTK) at its N-terminus 604. In the example, the polymerase is also functionalized at site Try 521 605 using a non-canonical azido functionalized amino acid to which a second SpyTag 605 is coupled by click chemistry. This attachment point is used because the C-terminus is near to the active site of the enzyme and cannot be used for attachment to electrodes. The functionalized polymerase D29 is incubated with the SpyCatcher-CTPR3 complex 606, 607 (as shown in FIG. 5), and size exclusion chromatography is used to select the desired reaction product comprising the polymerase attached to two CTPR3 arms. The electrodes are functionalized with cysteine-terminated SpyTag 608, 609, where the cysteines 610, 611 are bound to the metal electrodes. The CTPR3 functionalized polymerase is then incubated with the functionalized electrodes, forming the bridging complex. In some embodiments, successful formation of the desired bridge is indicated by a jump in current passing between the electrodes.

Figure 7:
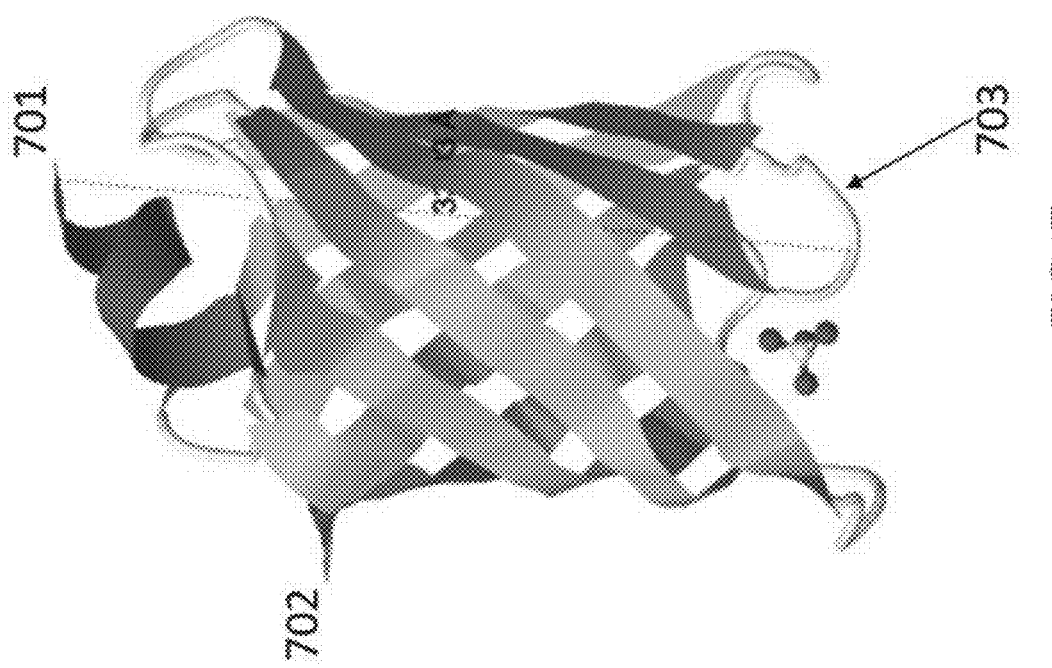
FIG. 7: Representative diagram of a β-barrel protein used as an adaptor polypeptide, according to one embodiment of the present disclosure.

In some embodiments, single structural elements, such as a β-barrel can also enclose a hydrophobic core, and thus also can be used as molecular wires. In the β-barrel configuration, a β-sheet folds into a cylinder with hydrophobic residues pointing inwards and with hydrophilic residues pointing outwards. An example is the synthetic protein RSC PDB structure 6CZJ, shown in FIG. 7. In these exemplary structures, the N- and C-termini (701 and 702, respectively) can be on the same end of the β-barrel. However, including a reactive peptide sequence or a non-canonical azido modified amino acid in a loop 703 at the other end of the barrel allows for long range current transport (3.3 nm for the structure shown in FIG. 7). In accordance with these embodiments, bioelectronic circuits comprising CTPR20 adaptor polypeptides can span electrode gaps approaching 40 nm, and are readily functionalized, thus greatly simplifying the construction of bioelectronic devices containing any protein-of-interest.

Figure 8:
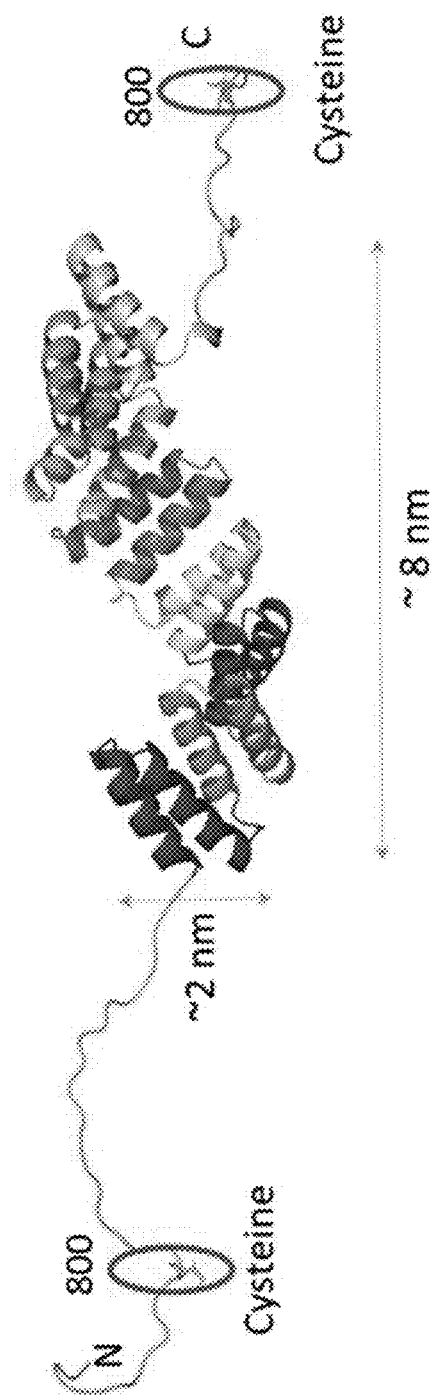
FIG. 8: Representative diagram of the structure of an adaptor polypeptide configuration comprising a CTPR8 polypeptide with cysteines engineered into the N- and C-termini as chemical anchors to metal electrodes, according to one embodiment of the present disclosure.

As demonstrated in FIG. 8, the conductivity of a CTPR8 wire was measured directly using a CTPR8 engineered to have the sequence disclosed as SEQ ID NO: 3 (MSYYHHHHHHSCSDYDIPTTENLYFQGAMGSAE-AWYNLGNAYYKQGDYDEAIEY YQKALELDPR-SAEAWYNLGNAYYKQGDYDEAIEYYQKALELDPR-SAEAWYNLGN AYYKQGDYDEAIEYYQKALELDPR-SAEAWYNLGNAYYKQGDYDEAIEYYQKLELD PRS-AEAWYNLGNAYYKQGDYDEAIEYYQKALELDPR-SAEAWYNLGNAYYKQGDY DEAIEYYQKALELDPR-SAEAWYNLGNAYYKQGDYDEAIEYYQKALELDPR-SAEAW YNLGNAYYKQGDYDEAIEYYQKALEL-DPRSAEAKQNLGNAKQKQGSCS). Referring to SEQ ID NO: 3, inserted cysteines are shown in bold font (C) and the HIS tag, which can be used for purification, is shown in italics (HHHHHH). A representative structure for this molecule is shown in FIG. 8.

Figure 9:
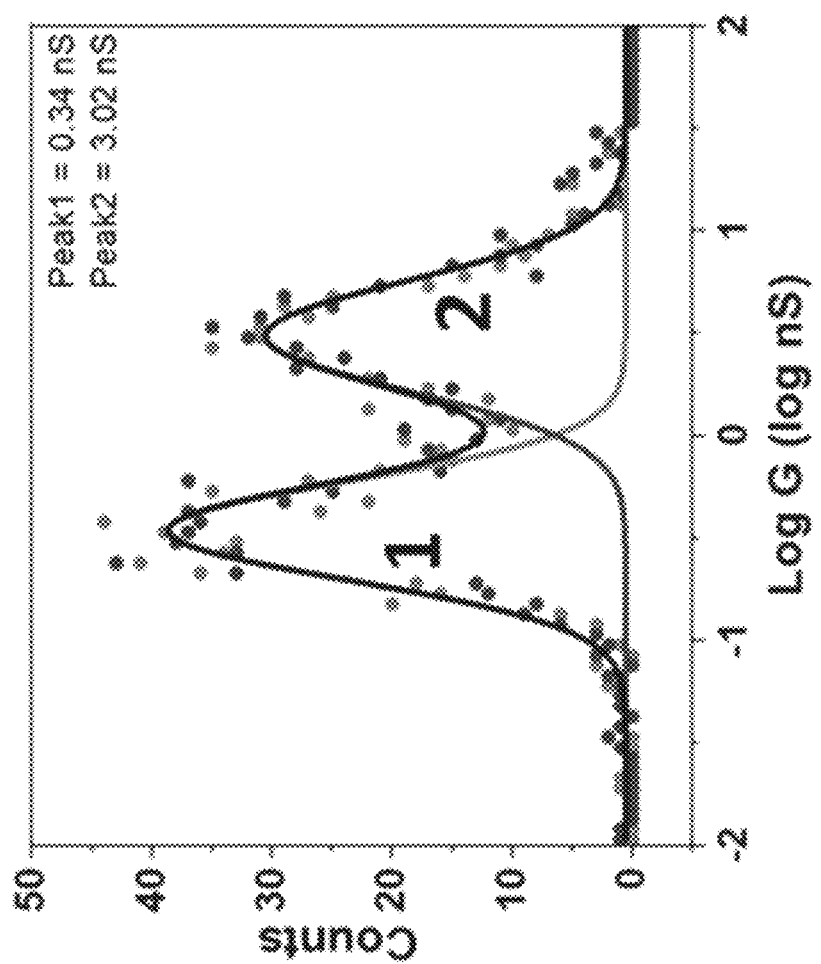
FIG. 9: Representative graph of the distribution of conductances measured in a bioelectronic device comprising a cysteine terminated CTPR8 adaptor polypeptide wire, according to one embodiment of the present disclosure.
Figure 10:
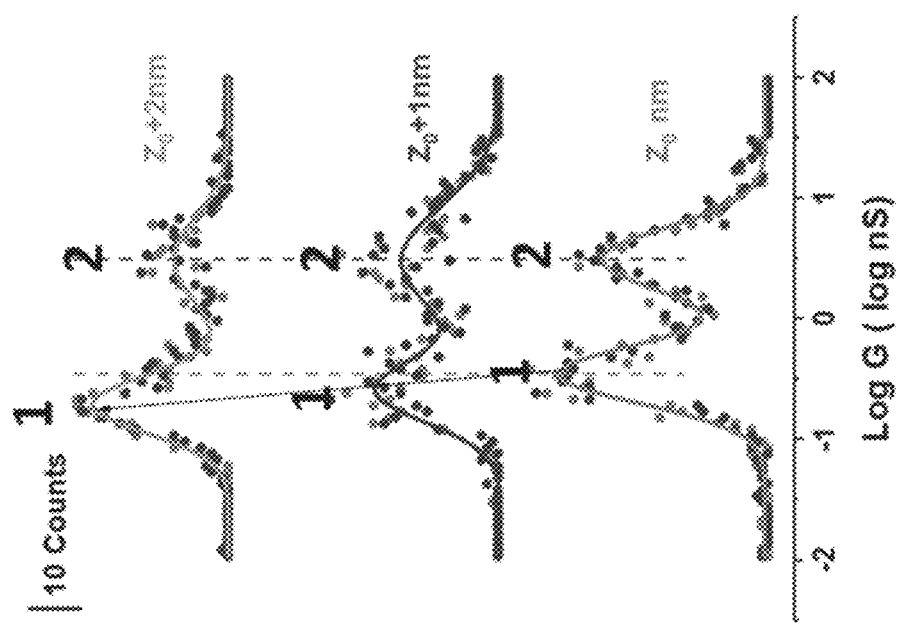
FIG. 10: Representative graphs demonstrating the dependence of conductance distribution on electrode gap size, according to one embodiment of the present disclosure. ($Z_0$ is the set-point gap of about 2.5 nm.)
Figure 11B:
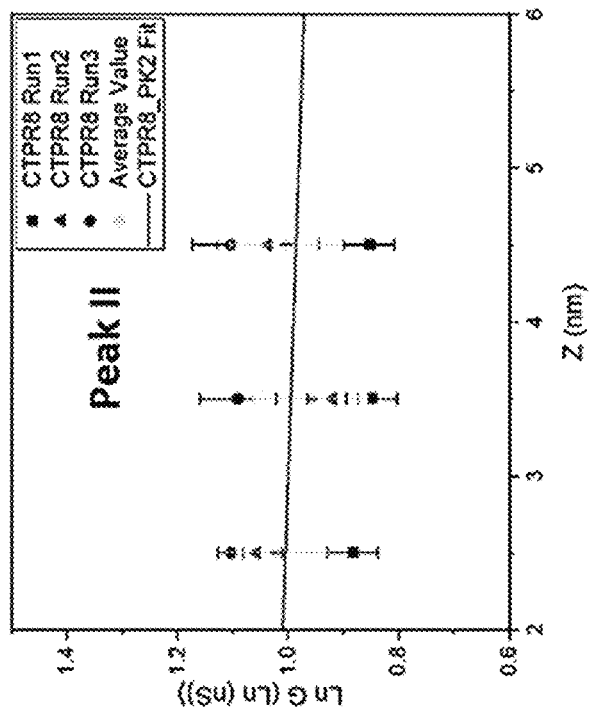
FIGS. 11A-11B: Representative graphs measuring conductance vs. electrode gap size for peak 1 (A) and peak 2(B), according to one embodiment of the present disclosure.
Figure 11A:
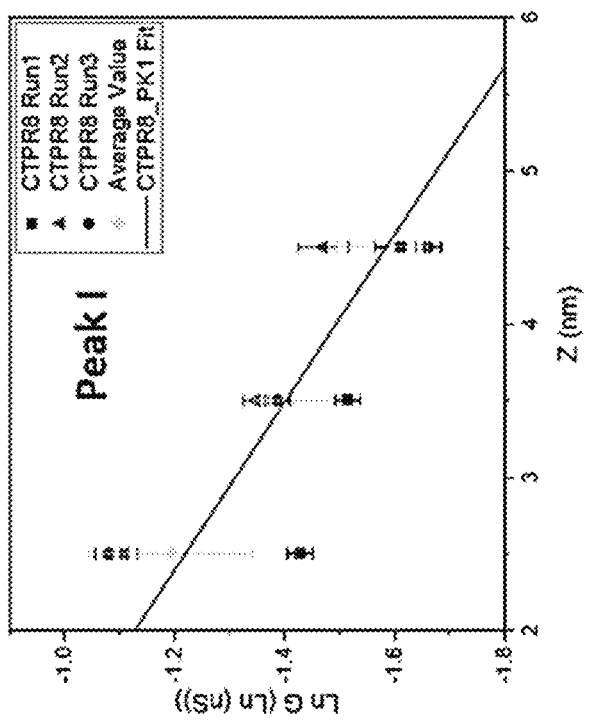

The conductivity of this molecular wire was measured using a scanning tunneling microscope with a Pd probe and a Pd substrate, operated in a buffered electrolyte. The measured distribution of conductances is shown in FIG. 9. There are two peaks, labeled "1" and "2." Peak 1 reaches a maximum at about 0.3 nS. Peak 2 reaches a maximum at about 3 nS. This distribution is similar to that observed for antibodies bound to epitopes on the electrodes, where the use of Fab fragments made from the same antibodies showed that peak 1 reflects one specific interaction (i.e. epitope-antibody interaction) and one non-specific interaction (i.e. hydrogen bonded interaction between the peptide on the probe and the antibody surface). Peak 2 reflects two specific interactions (i.e. epitope antibody at each of the two antibody heads). A consequence of this is that the value of peak 1 changes with the size of the electrode gap as different points along the molecule are contacted, whereas peak 2 maintains a constant value as the gap is changed. The same characteristic is observed in this case, as shown in FIG. 10. The value of peak 2 is unchanged as the gap is increased from the setpoint gap $Z_0$ (approximately 2.5 nm) to $Z_0+2$ nm (approximately 4.5 nm). In contrast, the value of peak 1 decreases significantly. Statistical data from 3 runs are summarized in FIG. 11. It can be seen that the conductance for peak 1 decreases significantly as the electrode gap is increased, whereas it does not change significantly for peak 2.

In some embodiments, the cysteine terminated molecule shown in FIG. 8 can serve as a ruler for measuring the effective size of electrode gaps. As is demonstrated in FIG. 10, the frequency of contacts decreases as the electrode gap is made larger, and conductance is lost entirely (for this exemplary molecule) when the gap approaches 8 nm. Therefore, the gap between electrodes may be determined by exposing a device to successively shorter CTPR molecules (i.e. the minimum length of molecule that can span the gap being given by the longest CTPR molecule that gives signals). This is a robust method for calibrating molecular electronic devices because the local binding geometry may not be able to accommodate the full gap size as determined by electron microscopy.

The CTPR adaptor polypeptides of the present disclosure are quite robust in structure and can accommodate significant alterations in amino acid sequence. As described herein, the aromatic residues (e.g., tyrosine, tryptophan, and phenylalanine) can be important for conductivity. For example, the conductance of a CTPR molecular wire may be increased substantially by inserting additional aromatic residues into the interior of the helix structures. This same ability to modify residues allows for alteration of the fluid-facing residues. Thus, these wires can also serve as sensors. For example, by placing glutamic acid residues on the exterior of the helices, a single-molecule pH sensor results, as the glutamate resides become deprotonated at low pH.

In accordance with these embodiments, the present disclosure also provides a molecular sensor device that includes a molecular wire having an adaptor polypeptide with one or more repeatable motifs (e.g., a consensus tetratricopeptide repeat) in which aromatic amino acid content has been increased so as to increase the conductivity of the molecule. In some embodiments, the present disclosure provides a method for determining the size of an electrode gap that includes exposing the gap to a series of cysteine-terminated CTPR molecular wires of decreasing length. In some embodiments, a molecular sensor of the present disclosure includes a first electrode and a second electrode bridged by a folded protein that presents an electrode binding site at each end and contains surface residues that undergo chemical changes in response to exposure to a target molecule.

Figure 12:
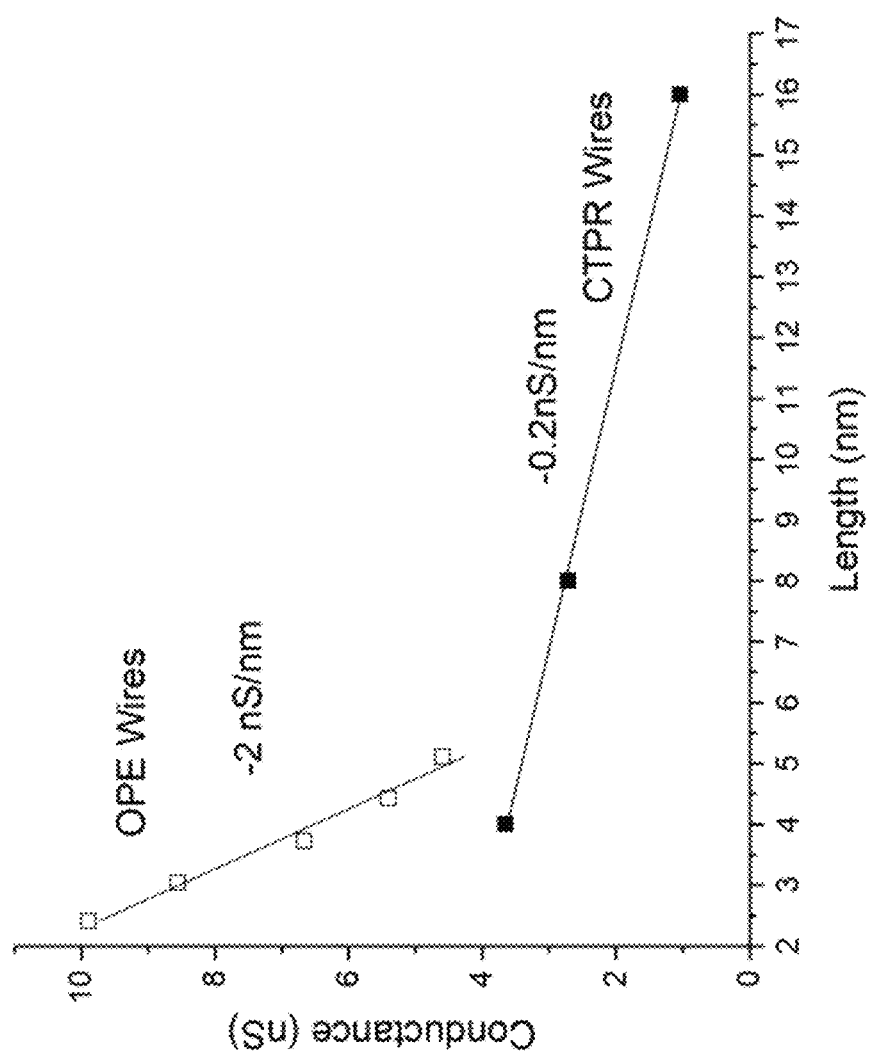
FIG. 12: Representative graph showing the conductances measured in a bioelectronic device comprising a CTPR4, a CTPR8, or a CTPR16 molecular wire (black squares). The line is a fit to a linear decrease of conductance of −0.2 nS/nm. The open squares show data for the measured conductances for a series of Oligo(p-phenyleneethynylene) (OPE) molecular wires. The decrease in conductance with length is −2 nS/nm (reduced by a factor of ten). Data are derived from the second peak in the conductance distributions in FIG. 9.

Referring to FIG. 12, bioelectronic devices were constructed with three different CTPR adaptor polypeptides synthesized with N- and C-terminated cysteines. FIG. 12 includes a representative graph showing the conductances measured in a bioelectronic device comprising a CTPR4, a CTPR8, or a CTPR16 molecular wire (black squares). The line is a fit to a linear decrease of conductance of −0.2 nS/nm. The open squares show data for the measured conductances for a series of Oligo(p-phenyleneethynylene) (OPE) molecular wires. The decrease in conductance with length is −2 nS/nm (reduced by a factor of ten). (Data are derived from the second peak in the conductance distributions in FIG. 9.) Measurements were made as a function of gap distance (Z) and repeated three times. The values of peak conductance for Peak 1 were fitted by: CTPR4: $Ln(G)=-0.67-0.12Z$; CTPR8: $Ln(G)=-0.76\pm0.08-(0.18\pm0.02)Z$; and CTPR16: $Ln(G)=-0.80\pm0.04-(0.14\pm0.02)Z$. Values of peak conductance for peak 2 were fitted by: CTPR4: $Ln(G)=1.30\pm0.10-(0.0115\pm0.03)Z$; CTPR8: $Ln(G)=1.03\pm0.10-(0.0096\pm0.03)Z$; and CTPR16: $Ln(G)=0.11\pm0.10-(0.0087\pm0.02)Z$. The peak 2 conductance was independent of gap size (within measurement error), yielding the following values for conductance for the three molecules: CTPR4: 3.7±0.3 nS; CTPR8: 2.8±0.05 nS; and CTPR16: 1.1±0.1 nS. These values were plotted against the crystallographic length of the molecules in FIG. 12. For comparison, the conductances of a series of Oligo(p-phenyleneethynylene) (OPE) molecular wires are also shown (open squares). OPE is widely used as a molecular wire, but, as can be seen, the decay of current with distance is significantly greater (e.g., by a factor of 10×) than for the CTPR wires. The OPE wires have a smaller contact resistance, and they can become more resistive after about 7 nm length. For distances beyond 5 nm, the CTPR wires of the present disclosure exhibit enhanced conductance.

Figure 13:
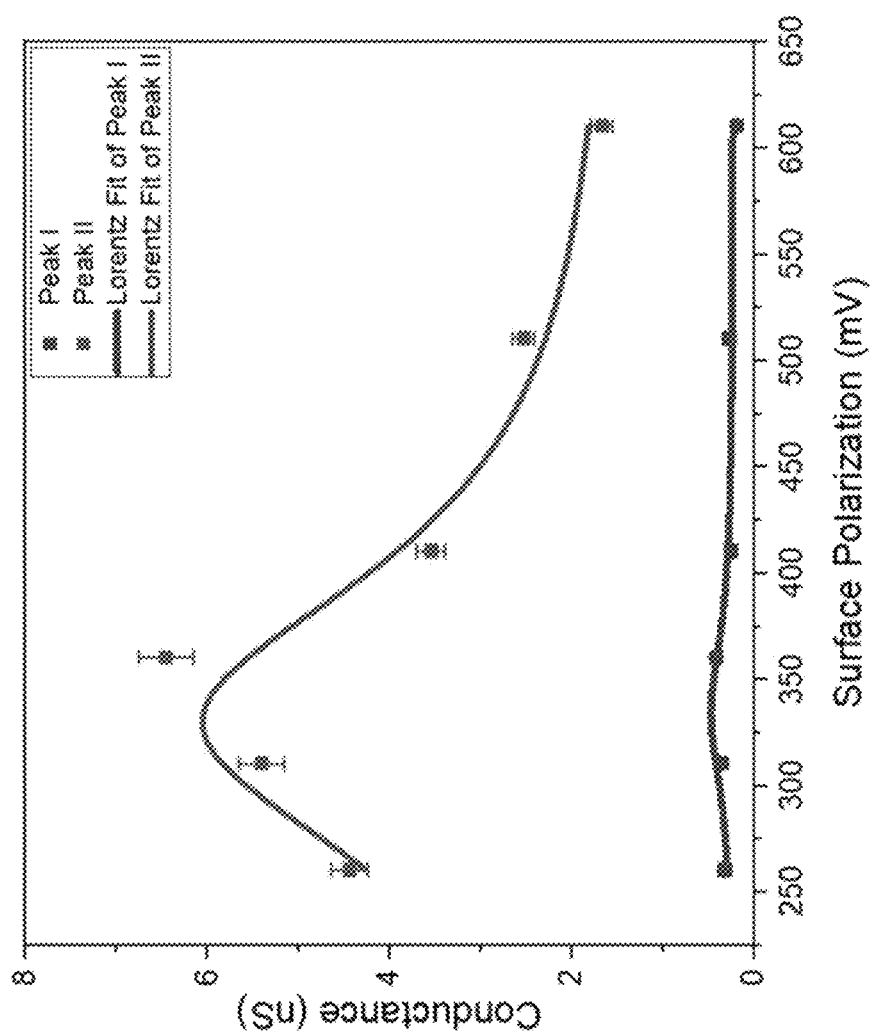
FIG. 13: Representative graph showing conductance as a function of surface potential (vs the Normal Hydrogen Electrode scale) for a bioelectronic device comprising CTPR8 wires. The lower curve corresponds to peak 1 in the conductance distribution, and the upper curve corresponds to peak 2, with reference to FIG. 9. The conductance peaks at around 300 mV on the NHE scale as observed for other protein conductors.
Figure 14:
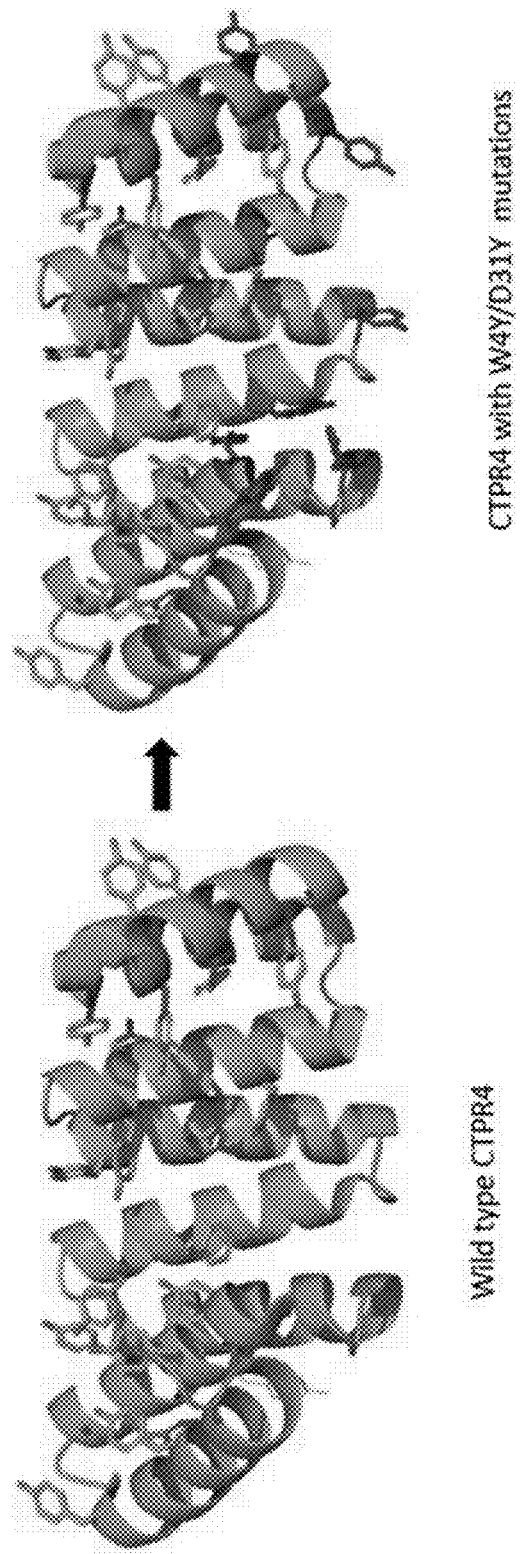
FIG. 14: Representative diagrams showing mutations that increase the tyrosine content of adaptor polypeptides. The crystal structure of the wild type CTPR4 is shown on the left with tyrosine residues highlighted. The structure of a mutant with tryptophan 4 (W4) mutated to tyrosine (Y) and aspartic acid 31 (D31) mutated to Y is shown on the right. (The mutated residues are shown in red.)

The dependence of conductance on electron energy has been previously measured for a series of proteins (see, e.g., Zhang, B., W. Song, J. Brown, R. Nemanich, and S. Lindsay, *Electronic Conductance Resonance in Non-Redox-Active Proteins*. Journal of the American Chemical Society, 2020. 142(13): p. 6432-6438), all of which show a conductance resonance when the electrodes are poised at +300 mV on the normal hydrogen electrode (NHE) scale. The CTPR adaptor polypeptides of the present disclosure exhibit similar characteristics. For example, FIG. 13 includes a representative graph showing conductance as a function of surface potential (vs. the Normal Hydrogen Electrode scale) for a bioelectronic device comprising CTPR8 molecular wires. The lower curve corresponds to peak 1 in the conductance distribution, and the upper curve corresponds to peak 2, with reference to FIG. 9. The conductance peaks at around 300 mV on the NHE scale as observed for other protein conductors. FIG. 13 demonstrated measured conductance for a CTPR8 protein (with N- and C-terminal cysteine connections) as a function of electrode potential. The peak at 300 mV is evident. Thus, conductance is mediated by the same mechanism as in other proteins, likely via resonance with electronic states of the tyrosine residues. This indicates that conductance may be further enhanced by enriching the tyrosine content of the proteins. For example, FIG. 14 includes representative diagrams showing mutations that increase the tyrosine content of adaptor polypeptides. The crystal structure of the wild type CTPR4 is shown on the left with tyrosine residues highlighted. The structure of a mutant with tryptophan 4 (W4) mutated to tyrosine (Y) and aspartic acid 31 (D31) mutated to Y is shown on the right. (The mutated residues are shown in red.) FIG. 14 shows that a significant increase in tyrosine content is possible without altering the structure of the CTPR.

Figure 15:
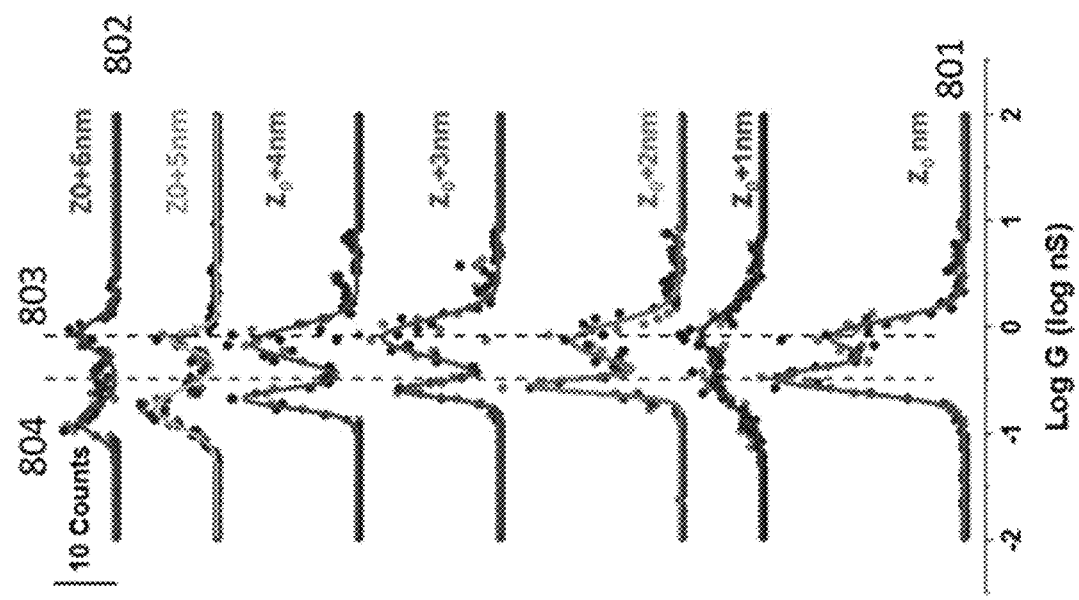
FIG. 15: Representative graphs of the distributions of conductances measured as a function of the electrode gap size for a bioelectronic device comprising a CTPR20 adaptor polypeptide wire, according to one embodiment of the present disclosure.

Referring to FIG. 15, CTPR wires were synthesized with cysteines incorporated into the N- and C-termini 800 as shown in FIG. 8 for CTPR8, but with different numbers of repeatable motifs. In this example, CTPR4, CTPR8, CTPR12, CTPR16, and CTPR20 molecular wires were synthesized. These configurations have lengths, based on crystallographic analysis, of about 4 nm, 6 nm, 12 nm, 16 nm, and 20 nm. The conductance was measures for each of these CTPR configurations, using repeated measurements on single molecules to extract the distribution of conductances for all possible contact geometries. An example of a set of measured distributions is given in FIG. 15. These data show the frequency with which a given conductance was measured vs. the logarithm of the conductance. These particular data correspond to CTPR20. Measurements were made in a scanning tunneling microscope. The set point $Z_0$ was an initial gap (approximately 2.5 nm or more) obtained by controlling for a 4 pA current at a bias of 100 mV. The probe was then withdrawn by the amount shown by each distribution. For example, in the bottom trace 801 in FIG. 15, the probe was not withdrawn so the distance was just $Z_0$. In the top trace 802, the probe was withdrawn by 6 nm so the distance was $Z_0+6$ nm. The distributions are shown displaced arbitrarily in the vertical direction for clarity. At a given probe distance, current-voltage curves are recorded until the probe catches a molecule, as indicated by a non-zero current flow, and the subsequent current voltage curves used to calculate molecular conductances for each molecule contacted. As observed in many similar experiments, two peaks 803 and 804 are observed in the distribution. The peak at the larger conductance 803 corresponds to two specific chemical contacts (the N- and C-terminal cysteines—800 in FIG. 8) so the conducting pathlength is similar. The peak at the lower conductance 804 corresponds to one specific contact and one non-specific contact at some point on the molecule. Since this second contact point will have a longer conduction path the larger the gap, its peak value shifts to smaller values as the gap is increased.

Figure 16:
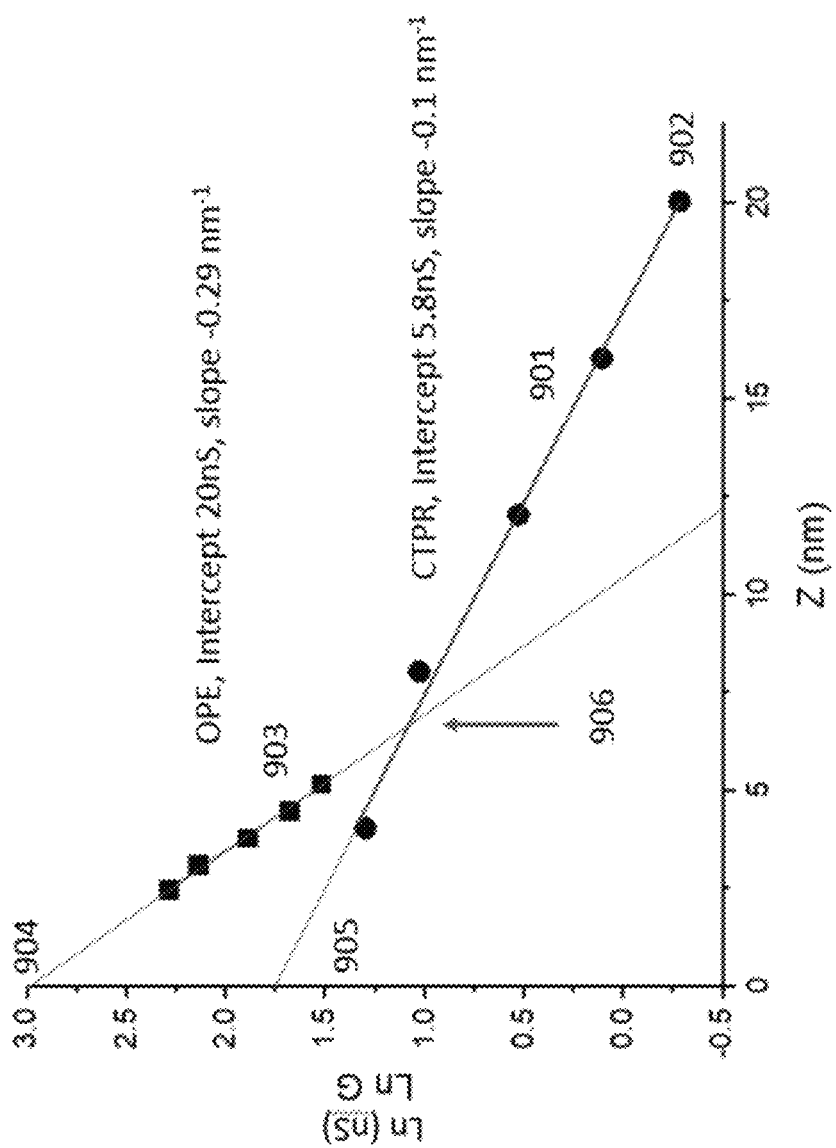
FIG. 16: Representative graph of the natural logarithm of the peak conductance corresponding to two specific contacts versus distance for a bioelectronic device comprising a CTPR adaptor polypeptide wires (squares), or oligophenyleneethynylene (OPE) wires (circles), according to one embodiment of the present disclosure. (Data for OPE are shown only for the long-range hopping regime.)

Measurements of the decay of electrical current as a function of molecular length illustrate the much greater utility and efficacy of bioelectronic devices comprising the adaptor polypeptides of the present disclosure over conventional molecular wires. For example, FIG. 16 shows (circles 901) how the natural log of the conductance corresponding to the larger peak 803 (FIG. 15) falls with distance. Note, however, that at 20 nm distance, the conductance is still 0.8 nS, 902, which is still a useful and effective conductance for molecular electronic components and circuits. The decay constant, 0.1 nm$^{-1}$, is very small, corresponding to a decay length of 10 nm. For comparison, the squares 903 show data for oligo(p-phenylene-ethynylene) OPE), an example of a state-of-the-art molecular wire. The contact conductance (conductance at zero length) at 20 ns 904 is much higher than that of the CTPR wires (5.8 nS) 905. However, the much larger decay constant, 0.29 nm$^{-1}$, means that the molecular wires comprising the CTPR adaptor polypeptides outperform OPE oligomers at distances greater than 7.5 nm 906.

Referring to FIG. 17, embodiments of the present disclosure also include methods for using the CTPR-based molecular wires as linkages between a protein-of-interest and two electrodes. For example, CTPR wires 1101 (shown as CTPR8, but other lengths can be used) are expressed with an N-terminal cysteine 1103 that couples the N-terminal region to the electrodes 1102. The C-terminal regions are expressed with an Avitag, biotinylated 1104 with the Bir-A enzyme. This biotinylated C-terminus is used to capture streptavidin 1105. The gap between the two streptavidin molecules is then bridged with a doubly-biotinylated polymerase 1106 (see, e.g., Zhang, B., H. Deng, S. Mukherjee, W. Song, X. Wang, and S. Lindsay, *Engineering an Enzyme for Direct Electrical Monitoring of Activity*. ACS Nano, 2020. 14: p. 1630-1638).

Figure 18:
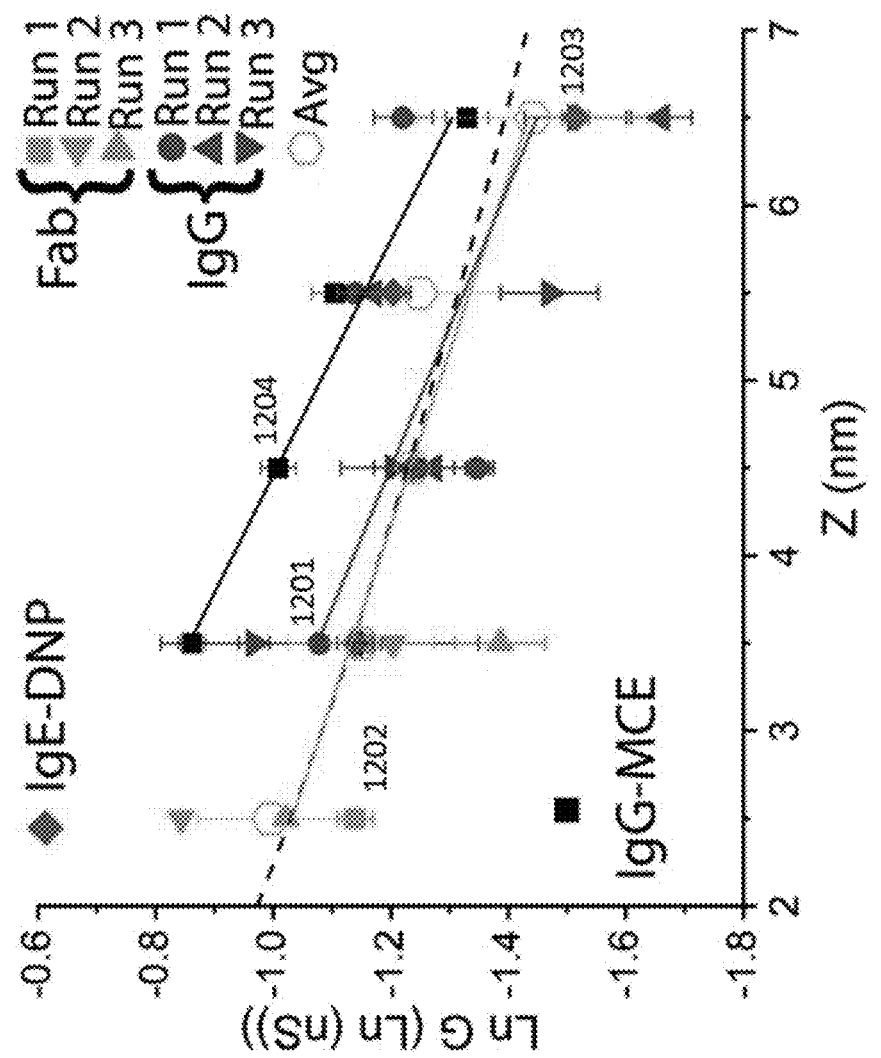
FIG. 18: Representative graph of conductances measured with respect to distance for several proteins exhibiting similar properties as the CTPR adaptor polypeptide wires of the present disclosure.

FIG. 18 includes representative data for the decay of the log of conductance with distance for an IgG antibody 1201, a Fab fragment 1202, and an IgE antibody 1203 (see, e.g., Zhang, B.; Lindsay, S., Electronic Decay Length in a Protein Molecule. *Nano letters* 2019, 19, 4017-4022). The lines are fits to an exponential decay, all with decay lengths of about 10 nm, similar to that observed with the CTPR molecular wires of the present disclosure. However, in this case, the measurements were made by making one specific contact (e.g., to an epitope attached to the electrodes) and one non-specific contact to some other point on the protein. Data obtained with an epitope functionalized substrate and a second electrode functionalized only with mercaptoethanol (MCE) to facilitate non-specific contacts to an IgG molecule are also shown 1204. These data demonstrate that the long decay length is not dependent on the specific type of contact used.

Figure 19:
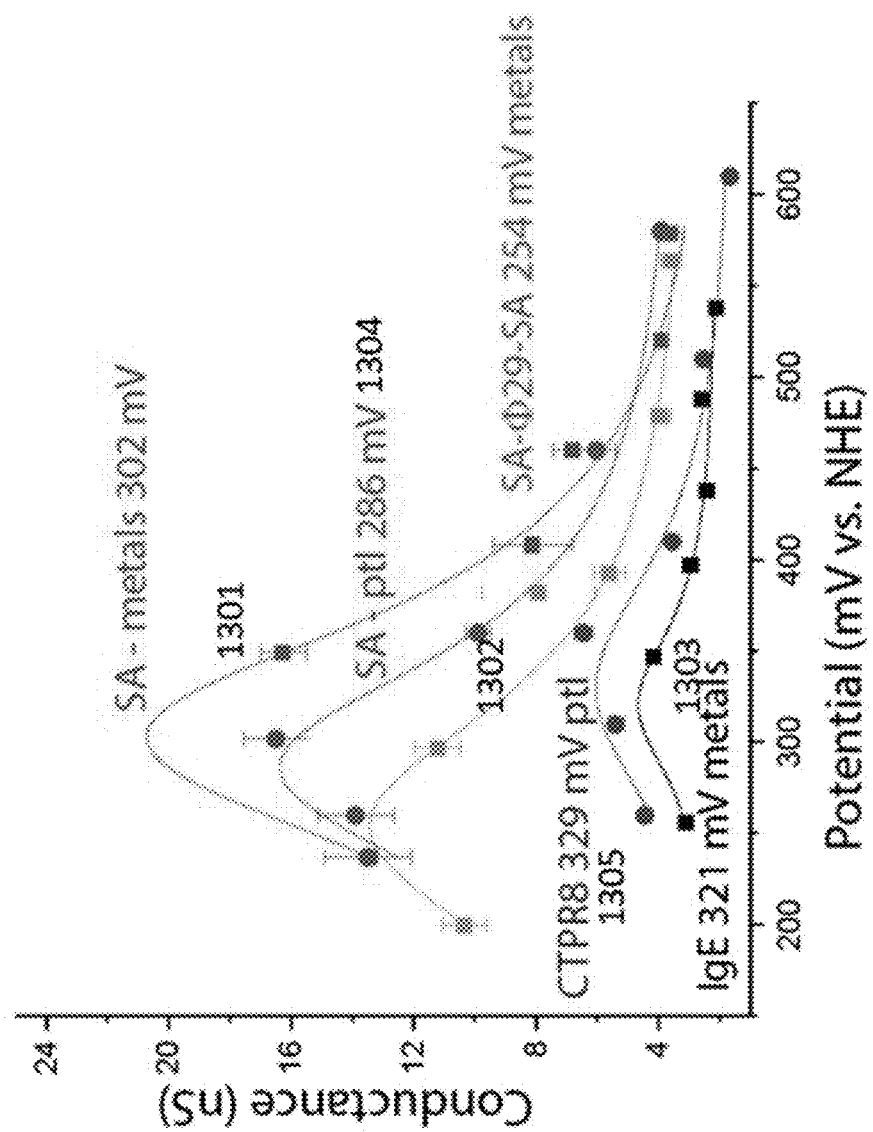
FIG. 19: Representative graph showing the change of conductance with electron injection energy for several proteins showing that a common mechanism is likely to be responsible for long range conduction, and that many proteins can serve as molecular wires, in addition to the CTPR adaptor polypeptide wires of the present disclosure.

Additionally, FIG. 19 shows measured values of conductance for a number of proteins as a function of the electron injection energy (based on the Normal Hydrogen Electrode—NHE-scale) made by the techniques described in Zhang, B., W. Song, J. Brown, R. Nemanich, and S. Lindsay, *Electronic Conductance Resonance in Non-Redox-Active Proteins*. Journal of the American Chemical Society, 2020. 142(13): p. 6432-6438. As shown, 1301 corresponds to data for streptavidin; 1302 corresponds to a complex of streptavidin and polymerase; and 1303 corresponds to an IgE molecule; all were measured using different metals for the electrodes. Additionally, 1304 corresponds to data for streptavidin measured by altering the potential of palladium electrodes with respect to a reference electrode; and 1305 includes data presented earlier for CTPR8, but reproduced here to show that a common resonance is responsible for the electronic properties of all these proteins. Taken together, these data demonstrate that many different proteins can be used as adaptor polypeptides for generating molecular wires; and, when modified so as to link an electrode to a protein-of-interest, these adaptor polypeptides can act as the linking elements, as described further herein. In particular, energy levels that most efficiently transport charge in the protein-based molecular wires are well matched to the energy levels that most efficiently transport charge in the protein sensor connected to the electrodes by these wires. This is not the case for wires composed, for example, of DNA or simple organic polymers such as oligophenyleneethynylene.

Referring to FIGS. 20A-20D, mutants of CTPR8-based molecular wires were expressed in which the tyrosine content was increased by the addition of two additional tyrosines (W4Y, D31Y). The sequence of the helix-turn-helix motif for the wild-type (WT) is shown in FIG. 20A, and the sequence of the W4Y, D3 1Y mutant is shown in FIG. 20B. (Tyrosines marked in yellow with the additional tyrosines pointed to by blue arrows.) Measured conductance distributions are shown in FIGS. 20C-20D. For example, FIG. 20C shows the distribution for the wildtype CTPR8 measured at an electrode gap of about 2.5 nm. The second peak in the distribution 1401 corresponds to the connection to two specific sites (the N- and C-terminal cysteines), and the corresponding peak conductance value is 3.63 nS. FIG. 20D shows the corresponding distribution for the W4Y/D31Y mutant. The second peak 1402 is increased to 4.68 nS. This represents a significant increase in conductance with respect to the increases in conductance that can be obtained by choosing the metal combinations used for the electrodes or using surface charges to change electron injection energy.

In accordance with the various embodiments described above, the bioelectronic devices and systems of the present disclosure generally include a first electrode and a second electrode that are configured for contact with a sample (e.g., biopolymer sample) to be analyzed. In some embodiments, such as when the electrodes are planar, the first and/or second electrode do not require a dielectric layer. In other embodiments, the first and/or second electrode can have a dielectric layer. In some embodiments, the first and/or second electrode comprise a metal selected from gold, silver, copper, platinum, palladium, and ruthenium (or any alloys thereof). In some embodiments, the metal is palladium. In some embodiments, the methods of the present disclosure include applying a voltage bias between the first and second electrodes that is 100 mV or less. It will be recognized by one of ordinary skill in the art based on the present disclosure that the bioelectronic devices and systems of the present disclosure, according to the various methods described herein, can be used to sequence DNA and RNA polymers by similar techniques (e.g., sequence RNA polymers using an RNA dependent RNA polymerase and four different ribonucleotides each carrying a distinctive charge).

In some embodiments, the gap between the first and second electrode is a width of about 1.0 nm to about 50.0 nm. In some embodiments, the gap between the first and second electrode is a width of about 1.0 nm to about 40.0 nm. In some embodiments, the gap between the first and second electrode is a width of about 1.0 nm to about 30.0 nm. In some embodiments, the gap between the first and second electrode is a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm. As provided herein, bioelectronic devices and systems of the present disclosure include an adaptor polypeptide(s) that stabilize a protein-of-interest within the gap between a first and second electrode.

In some embodiments, the protein-of-interest can include, but is not limited to, a polymerase, a nuclease, a proteasome, a glycopeptidase, a glycosidase, a kinase and an endonuclease. In some embodiments, the protein-of-interest is a polymerase. In some embodiments, the polymerase can be attached to one electrode in one embodiment and to both electrodes in another embodiment. The polymerase can be attached to the electrode(s) either directly or indirectly. In some embodiments, the polymerase is attached to the electrode(s) via a linker, including but not limited to, a biotin-streptavidin linker, a SpyTag-SpyCatcher linker, a halotag linker, and a thiolated CTPR linker. In some embodiments, the polymerase is attached to the electrode indirectly via interactions with a ligand attached to the electrode. In some embodiments, the polymerase is modified to incorporate a ligand-binding site. In some embodiments, the polymerase is a biotinylated polymerase. In some embodiments, the polymerase comprises an Avitag. In some embodiments, the polymerase is a biotinylated polymerase and is attached to the electrode via streptavidin. In some embodiments, the polymerase is modified to incorporate an amino acid residue that allows for click-chemistry attachment of other chemical groups to the electrodes (e.g., 4-Azido-L-phenylalanine.). In some embodiments, the exonuclease activity of the polymerase is disabled. In some embodiments, linker is attached to a region of the polymerase that is inactive. When the polymerase is attached to both electrodes, the two attachment points must not move relative to each other, when the polymerase undergoes open-to-closed conformational changes. The crystal structures of many polymerases are currently available (see, e.g., www.rcsb.org) in both open and closed forms.

In accordance with these embodiments, the present disclosure also provides bioelectronic devices and systems in which the charge on a protein-of-interest is altered in order to modulate the overall conductance of a protein complex (e.g., a protein-of-interest and corresponding linker). For example, the conductance of a given protein complex in a bioelectronic device configured with platinum electrodes can be modulated (e.g., increased) to be similar to the conductance provided by gold electrodes by altering the charge of the protein complex (e.g., shifting the potential). Thus, embodiments of the present disclosure include a bioelectronic device that includes a first electrode and a second electrode separated by a gap, and a protein (e.g., a polymerase) attached to the first and second electrodes via a linker comprising a distinctive electrical charge. In some embodiments, the distinctive electrical charge modulates conductance through the protein in a manner that enhances the function of the bioelectronic device (e.g., sequencing of a biopolymer).

In some embodiments, the linker used to generate a bioelectronic device of the present disclosure includes a peptide or polypeptide. In some embodiments, the linker comprises streptavidin. In some embodiments, the linker comprises streptavidin that has been modified to have a positive or negative charge (e.g., with polyglutamate). In some embodiments, the protein-of-interest is biotinylated. In some embodiments, the linker comprises a distinctive negative charge. In some embodiments, the distinctive negative charge is conferred by addition of a glutamate moiety, an aspartate moiety, or a combination thereof (including derivatives, variants, and polymers), coupled to the streptavidin. In some embodiments, the distinctive negative charge increases the conductance through the protein. In some embodiments, the linker comprises a distinctive positive charge. In some embodiments, the distinctive positive charge is conferred by addition of an arginine moiety, a histidine moiety, a lysine moiety, or a combination thereof (including derivatives, variants, and polymers), coupled to the streptavidin. In some embodiments, the distinctive positive charge increases or decreases the conductance through the protein.

Charge modulation of conductance confers several advantages, including but not limited to, increasing the conductance of a complex using electrodes whose rest potentials place them far from the peak of the conductance vs. potential curve. Peak conductances can be obtained with gold or gold-palladium combinations of electrodes, but gold has various limitations as an electrode material in many semiconductor processes. Therefore, it can be advantageous to use other metals, such as Pt or Pd or other noble metals, but doing so can lead to a reduced signal. Thus, as provided herein, the signal can be restored or enhanced by altering the charge of the protein complex (e.g., using a modified streptavidin as a linker). While this effect applies to streptavidin linker molecules, it readily can be applied to any other type of protein molecule used as a connector/linker, as would be recognized by one of ordinary skill in the art based on the present disclosure.

As persons of ordinary skill in the art will readily recognize and appreciate after having benefited from the teachings of the present disclosure, the methods described herein can be used with any bioelectronic device that senses the duration of the open and closed states of an enzyme (e.g., polymerase). Exemplary devices include, but are not limited to, the bioelectronic devices and systems disclosed in U.S. Pat. No. 10,422,787 and PCT Appln. No. PCT/US2019/032707, both of which are herein incorporated by reference in their entirety and for all purposes.

In accordance with these embodiments, the devices and systems of the present disclosure include a bioelectronic device comprising a first electrode and a second electrode separated by a gap, a protein attached to the first and second electrodes via a linker, and at least one adaptor polypeptide coupled to the protein, thereby stabilizing the protein within the gap. In some embodiments, the bioelectronic device comprises a single adaptor polypeptide coupled to the protein and at least one electrode. In some embodiments, the bioelectronic device comprises two adaptor polypeptides coupled to the protein and the two electrodes. In some embodiments, the bioelectronic device comprises more than two adaptor polypeptides coupled to the two electrodes. The precise configuration of the protein and adaptor polypeptides with respect to the first and second electrodes can vary, as described further herein. The precise configuration used in a particular bioelectronic device depends on a variety of factors, including but not limited to, the specific protein-of-interest, the presence/absence of linkers, the size of the gap between the electrodes, the amount of conductance required, and the like.

In some embodiments, the adaptor polypeptide comprises a hydrophobic core. In some embodiments, the adaptor polypeptide comprises a hydrophilic exterior. In some embodiments, the adaptor polypeptide is capable of folding into a stable conformation such that the hydrophobic core faces the inside of the polypeptide and the hydrophilic exterior faces the outside of the polypeptide.

In some embodiments, the adaptor polypeptide(s) comprises a repeatable motif, such that the size or length of the adaptor polypeptide(s) can be adjusted or engineered based on the size of an electrode gap and/or a protein-of-interest, among other factors. In some embodiments, the number of repeatable motifs is adjustable based on the size of the gap between the first and second electrodes. In some embodiments, the at least one repeatable motif comprises an α-helix and/or a β-sheet, and any combination thereof. In some embodiments, the repeatable motif includes at least two or more α-helices. In some embodiments, the repeatable motif includes at least two or more β-sheets. In some embodiments, the repeatable motif includes one or more β-barrels.

In some embodiments, the adaptor polypeptide includes at least one aromatic amino acid positioned within its hydrophobic core. In some embodiments, the adaptor polypeptide includes at least one amino acid substitution from a non-aromatic amino acid to an aromatic amino acid positioned within its hydrophobic core. In some embodiments, the adaptor polypeptide includes at least one amino acid substitution from an aromatic amino acid to a non-aromatic amino acid positioned within its hydrophobic core. In some embodiments, the at least one aromatic amino acid is tyrosine, tryptophan, or phenylalanine. In some embodiments, modulating the number of aromatic amino acids within the hydrophobic core of the adaptor polypeptide alters the conductance of a bioelectronic device.

In some embodiments, one or more amino acid residues on the adaptor polypeptide can be functionalized. In some embodiments, the adaptor polypeptide comprises a C-terminal and/or N-terminal cysteine residue. In some embodiments, the adaptor polypeptide is directly coupled to at least one of the first and second electrodes. In some embodiments, the adaptor polypeptide is coupled to at least one of the first and second electrodes via a linker. In some embodiments, the linker is selected from the group consisting of a biotin-streptavidin linker, a SpyTag-SpyCatcher linker, a halotag linker, and a thiolated CTPR linker. In some embodiments, the adaptor polypeptide is directly coupled to the protein. In some embodiments, the adaptor polypeptide is coupled to the protein electrodes via a linker. In some embodiments, the linker is selected from the group consisting of a biotin-streptavidin linker, a SpyTag-SpyCatcher linker, a halotag linker, and a thiolated CTPR linker.

In some embodiments, the presence of the adaptor polypeptide in a bioelectronic device reduces conductance decay as the gap between the first and second electrodes increases. As would be recognized by one of ordinary skill in the art based on the present disclosure, many different polypeptides and proteins can be used as an adaptor polypeptide in the context of the bioelectronic devices described herein. Generally, an adaptor polypeptide comprises a hydrophobic core, a hydrophilic exterior, at least one repeatable motif to facilitate size adjustment, and can form a stable conformation. In some embodiments, the adaptor polypeptide comprises a consensus tetratricopeptide repeat (CTPR) adaptor polypeptide. In some embodiments, the CTPR is selected from the group consisting of CTPR1, CTPR2, CTPR3, CTPR4, CTPR5, CTPR6, CTPR7, CTPR8, CTPR9, CTPR10, CTPR11, CTPR12, CTPR13, CTPR14, CTPR15, CTPR16, CTPR17, CTPR18, CTPR19, CTPR20, and any derivatives or variants thereof. In some embodiments, the device comprises two CTPR adaptor polypeptides, and the two CTPR adaptor polypeptides are the same size. In some embodiments, the device comprises two CTPR adaptor polypeptides, and each CTPR adaptor polypeptide is a different size. In some embodiments, the linker and/or the at least one adaptor polypeptide is coupled to an inactive region of the protein-of-interest.

In some embodiments, the linker comprises a distinctive negative charge. In some embodiments, the distinctive negative charge is conferred by addition of a glutamate moiety, an aspartate moiety, or a combination thereof, coupled to the linker. In some embodiments, the distinctive negative charge increases conductance through the protein. In some embodiments, the linker comprises a distinctive positive charge. In some embodiments, the distinctive positive charge is conferred by addition of an arginine moiety, a histidine moiety, a lysine moiety, or a combination thereof, coupled to the linker. In some embodiments, the distinctive positive charge increases or decreases conductance through the protein.

Embodiments of the present disclosure also include a system comprising a plurality of the devices described herein. In some embodiments, the systems of the present disclosure are used for direct electrical measurement of protein activity. In accordance with these embodiments, the system includes any of the bioelectronic devices described herein, a means for introducing an analyte capable of interacting with the protein, a means for applying a voltage bias between the first and second electrodes that is 100 mV or less, and a means for monitoring fluctuations that occur as the chemical entity interacts with the protein.

Embodiments of the present disclosure also include an array comprising a plurality of any of the bioelectronic devices described herein. In some embodiments, the array includes a means for introducing an analyte capable of interacting with the protein, a means for applying a voltage bias between the first and second electrodes that is 100 mV or less, and a means for monitoring fluctuations that occur as the chemical entity interacts with the protein. The array can be configured in a variety of ways, as would be appreciated by one of ordinary skill in the art based on the present disclosure.

Embodiments of the present disclosure also include a method for direct electrical measurement of protein activity. In accordance with these embodiments, the method includes introducing an analyte capable of interacting with the protein to any of the bioelectronic devices described herein, applying a voltage bias between the first and second electrodes that is 100 mV or less, and observing fluctuations in current between the first and second electrodes that occur when the analyte interacts with the protein. In some embodiments, the analyte is a biopolymer, such as, but not limited to, a DNA molecule, an RNA molecule, a peptide, a polypeptide, or a gly can.

3. Methods of Use

Embodiments of the present disclosure also include methods of measuring electronic conductance through a protein using any of the devices and systems described herein. In accordance with these embodiments, the present disclosure includes methods for direct electrical measurement of protein activity. In some embodiments, the method includes introducing an analyte capable of interacting with the protein to any of the bioelectronic devices described herein, applying a voltage bias between the first and second electrodes that is 100 mV or less, and observing fluctuations in current between the first and second electrodes that occur when the analyte interacts with the protein. In some embodiments, the analyte is a biopolymer selected from the group consisting of a DNA molecule, an RNA molecule, a peptide, a polypeptide, and a glycan. In some embodiments, methods of the present disclosure include use of the devices and systems described herein to sequence a biopolymer. In some embodiments, the present disclosure includes methods for sequencing a polynucleotide using a bioelectronic device that obtains a bioelectronic signature of polymerase activity based on current fluctuations as complementary nucleotide-polyphosphate monomers are incorporated into the template polynucleotide.

As described further herein, the devices, systems, and methods of the present disclosure can be used to generate a bioelectronic signature of an enzyme-of-interest, which can be used to determine the sequence of any biopolymer (e.g., polynucleotide). In some embodiments, the enzyme-of-interest can be a polymerase, and various aspects of a bioelectronic signature of a polymerase as it adds nucleotide monomers to a template polynucleotide strand can be used to determine the sequence of that template polynucleotide. For example, a bioelectronic signature of polymerase activity can be based on current fluctuations as each complementary nucleotide monomer is incorporated into the template polynucleotide. In some embodiments, the bioelectronic device used to generate a bioelectronic signature comprises a polymerase functionally coupled to both a first electrode and a second electrode using the adaptor polypeptides of the present disclosure. The term "nucleotide" generally refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

As one of ordinary skill in the art will readily recognize and appreciate after having benefited from the teachings of the present disclosure, the methods described herein can be used with any bioelectronic device that senses the duration of the open and closed states of an enzyme (e.g., polymerase). Exemplary devices include, but are not limited to, the bioelectronic devices and systems disclosed in U.S. Pat. No. 10,422,787 and PCT Appln. No. PCT/US2019/032707, both of which are herein incorporated by reference in their entirety and for all purposes. Additionally, it will be readily recognized and appreciated by those of ordinary skill in the art based on the present disclosure that the forgoing embodiments apply equally to (and include) sequencing RNAs with the substitution of rNTPs for dNTPs and the use of an RNA polymerase.

Further, one of ordinary skill in the art would readily recognize and appreciate that the methods described herein can be used in conjunction with other methods involving the sequencing of a biopolymer. In particular, the various embodiments disclosed in PCT Application No. PCT/US21/19428, which is herein incorporated by reference in its entirety, describes the interpretation of current fluctuations generated by a DNA polymerase as it actively extends a template, and how signal features (e.g., bioelectronic signature) may be interpreted in terms of the nucleotide being incorporated, and thus, how these signals can read the sequence of the template. This approach utilizes features of the signal that vary in time. For example, the time that the polymerase stays in a low current state reflects the concentration of the nucleotidetriphosphate in solution. If the concentration of a particular nucleotide triphosphate is low, then the polymerase must stay open for a longer time in order to capture the correct nucleotide, and since the open conformation of the polymerase corresponds to a lower current, the dip in current associated with the open state lasts for longer. Additionally, the various embodiments disclosed in PCT Application No. PCT/US20/38740, which is herein incorporated by reference in its entirety, describes how the base-stacking polymerization rate constant differences are reflected in the closed-state (high current states) so that the duration of these states may also be used as an indication of which one of the four nucleotides is being incorporated. It can be desirable to be able to use the amplitude of the signal as yet an additional contribution to determining sequence. Further, the various embodiments disclosed in PCT Application No. PCT/US21/17583, which is herein incorporated by reference in its entirety, describes methods that utilize a defined electrical potential to maximize electrical conductance of a protein-of-interest (e.g., polymerase), which can serve as a basis for the fabrication of enhanced bioelectronic devices for the direct measurement of protein activity. Additionally, the various embodiments disclosed in PCT Application No. PCT/US21/30239, which is herein incorporated by reference in its entirety, describes methods for sequencing a polynucleotide using a bioelectronic device that obtains a bioelectronic signature of polymerase activity based on current fluctuations as complementary nucleotide-polyphosphate monomers having distinctive charges are incorporated into the template polynucleotide.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

Sequences. The following sequences are referred to in the present disclosure and/or are used in accordance with the various embodiments disclosed herein.

```
                                              (SEQ ID NO: 1)
GAMDPGNSAEAWYNLGNAYYKQGDYDEAIEYYQKALELDPNNAEAWY

NLGNAYYKQGDYDEAIEYYQKALELDPNNAEAWYNLGNAYYKQGDYDE

AIEYYQKALELDPNNAEAKQNLGNAKQKQG. See, also,

FIG. 1.

(SEQ ID NO: 2)
AHIVMVDAYKPTK.

(SEQ ID NO: 3)
MSYYHHHHHHSCSDYDIPTTENLYFQGAMGSAEAWYNLGNAYYKQGDY

DEAIEYYQKALELDPRSAEAWYNLGNAYYKQGDYDEAIEYYQKALELD

PRSAEAWYNLGNAYYKQGDYDEAIEYYQKALELDPRSAEAWYNLGNAY

YKQGDYDEAIEYYQKLELDPRSAEAWYNLGNAYYKQGDYDEAIEYYQK

ALELDPRSAEAWYNLGNAYYKQGDYDEAIEYYQKALELDPRSAEAWYN

LGNAYYKQGDYDEAIEYYQKALELDPRSAEAWYNLGNAYYKQGDYDEA

IEYYQKALELDPRSAEAKQNLGNAKQKQGSCS.

(SEQ ID NO: 4)
GSAEAWYNLGNAYYQGDYDEAIEYYQKALELDPRSAEAWYNLGNAYYK

QGDYDEAIEYYQKALELDPRS.

(SEQ ID NO: 5)
GSAEAYYNLGNAYYQGDYDEAIEYYQKALELYPRSAEAWYNLGNAYYK

QGDYDEAIEYYQKALELDPRS.
```

What is claimed is:

1. A bioelectronic device comprising:
   a first electrode and a second electrode separated by a gap;
   a protein attached to the first and second electrodes via a linker; and
   at least one adaptor polypeptide coupled to the protein, thereby stabilizing the protein within the gap;
   wherein the at least one adaptor polypeptide comprises at least one repeatable motif, wherein the number of repeatable motifs is adjustable based on the size of the gap between the first and second electrodes.

2. The bioelectronic device of claim 1, wherein the at least one adaptor polypeptide comprises two adaptor polypeptides, each adaptor polypeptide coupled to the protein at difference positions on the protein.

3. The bioelectronic device of claim 1, wherein the at least one adaptor polypeptide comprises a hydrophobic core.

4. The bioelectronic device of claim 1, wherein the at least one adaptor polypeptide comprises a hydrophilic exterior.

5. The bioelectronic device of claim 1, wherein the at least one repeatable motif comprises an α-helix and/or a β-sheet.

6. The bioelectronic device of claim 1, wherein the at least one repeatable motif comprises at least two α-helices.

7. The bioelectronic device of claim 1, wherein the at least one repeatable motif comprises a β-barrel.

8. The bioelectronic device of claim 1, wherein the at least one adaptor polypeptide comprises at least one aromatic amino acid positioned within its hydrophobic core.

9. The bioelectronic device of claim 8, wherein the at least one aromatic amino acid is tyrosine, tryptophan, or phenylalanine.

10. The bioelectronic device of claim 1, wherein the at least one adaptor polypeptide comprises at least one amino acid substitution from a non-aromatic amino acid to an aromatic amino acid positioned within its hydrophobic core.

11. The bioelectronic device of claim 1, wherein the at least one adaptor polypeptide comprises a C-terminal and/or N-terminal cysteine residue.

12. The bioelectronic device of claim 1, wherein the at least one adaptor polypeptide is directly coupled to at least one of the first and second electrodes.

13. The bioelectronic device of claim 1, wherein the at least one adaptor polypeptide is coupled to at least one of the first and second electrodes via a linker.

14. The bioelectronic device of claim 1, wherein the linker is selected from the group consisting of a biotin-streptavidin linker, a spytag-spycatcher linker, a halotag linker, a thiolated linker, a thiolated tetratricopeptide repeat (TPR) linker, and a thiolated consensus tetratricopeptide repeat (CTPR) linker.

15. The bioelectronic device of claim 1, wherein the at least one adaptor polypeptide is directly coupled to the protein.

16. The bioelectronic device of claim 1, wherein the at least one adaptor polypeptide is coupled to the protein electrodes via a linker.

17. The bioelectronic device of claim 1, wherein the at least one adaptor polypeptide comprises a consensus tetratricopeptide repeat (CTPR) adaptor polypeptide.

18. The bioelectronic device of claim 17, wherein the CTPR is selected from the group consisting of CTPR1, CTPR2, CTPR3, CTPR4, CTPR5, CTPR6, CTPR7, CTPR8, CTPR9, CTPR10, CTPR11, CTPR12, CTPR13, CTPR14, CTPR15, CTPR16, CTPR17, CTPR18, CTPR19, CTPR20, and any derivatives or variants thereof.

19. The bioelectronic device of claim 1, wherein the device comprises two CTPR adaptor polypeptides, and wherein the two CTPR adaptor polypeptides are the same size.

20. The bioelectronic device of claim 1, wherein the device comprises two CTPR adaptor polypeptides, and wherein each CTPR adaptor polypeptide is a different size.

21. The bioelectronic device of claim 1, wherein presence of the adaptor polypeptide reduces conductance decay as the gap between the first and second electrodes increases.

22. The bioelectronic device of claim 1, wherein the protein is selected from the group consisting of a polymerase, a nuclease, a proteasome, a glycopeptidase, a glycosidase, a kinase and an endonuclease.

23. The bioelectronic device of claim 1, wherein the linker and/or the at least one adaptor polypeptide is coupled to an inactive region of the protein.

24. The bioelectronic device of claim 1, wherein the protein and the first and second electrodes are biotinylated, and wherein the linker comprises a streptavidin molecule comprising at least two biotin binding sites.

25. The bioelectronic device of claim 1, wherein the linker comprises a distinctive negative charge.

26. The bioelectronic device of claim 25, wherein the distinctive negative charge is conferred by addition of a glutamate moiety, an aspartate moiety, or a combination thereof, coupled to the linker.

27. The bioelectronic device of claim 25, wherein the distinctive negative charge increases conductance through the protein.

28. The bioelectronic device of claim 25, wherein the linker comprises a distinctive positive charge.

29. The bioelectronic device of claim 28, wherein the distinctive positive charge is conferred by addition of an arginine moiety, a histidine moiety, a lysine moiety, or a combination thereof, coupled to the linker.

30. The bioelectronic device of claim 28, wherein the distinctive positive charge increases or decreases conductance through the protein.

31. The bioelectronic device of claim 1, wherein the first and/or the second electrode comprises gold, palladium, platinum, silver, copper, or any alloys thereof.

32. The bioelectronic device of claim 1, wherein the device comprises a dielectric layer at least partially covering a surface of the first and/or second electrode.

33. The bioelectronic device of claim 1, wherein the first electrode and second electrode are positioned so that about a 1 nm to about a 50 nm gap is formed between the two electrodes.

34. A method for direct electrical measurement of protein activity, the method comprising:
(a) introducing an analyte capable of interacting with the protein of the bioelectronic device of claim 1;
(b) applying a voltage bias between the first and second electrodes that is 100 mV or less; and
(c) observing fluctuations in current between the first and second electrodes that occur when the analyte interacts with the protein.

35. The method of claim 34, wherein the analyte is a biopolymer selected from the group consisting of a DNA molecule, an RNA molecule, a peptide, a polypeptide, and a glycan.

* * * * *

SEQUENCE LISTING

<160> NUMBER OF SEQ ID NOS: 5

<210> SEQ ID NO 1
<211> LENGTH: 125
<212> TYPE: PRT
<213> ORGANISM: Artificial sequence
<220> FEATURE:
<223> OTHER INFORMATION: Synthetic

<400> SEQUENCE: 1

Gly Ala Met Asp Pro Gly Asn Ser Ala Glu Ala Trp Tyr Asn Leu Gly
1               5                   10                  15

Asn Ala Tyr Tyr Lys Gln Gly Asp Tyr Asp Glu Ala Ile Glu Tyr Tyr
                20                  25                  30

Gln Lys Ala Leu Glu Leu Asp Pro Asn Asn Ala Glu Ala Trp Tyr Asn
            35                  40                  45

Leu Gly Asn Ala Tyr Tyr Lys Gln Gly Asp Tyr Asp Glu Ala Ile Glu
        50                  55                  60

Tyr Tyr Gln Lys Ala Leu Glu Leu Asp Pro Asn Asn Ala Glu Ala Trp
65                  70                  75                  80

Tyr Asn Leu Gly Asn Ala Tyr Tyr Lys Gln Gly Asp Tyr Asp Glu Ala
                85                  90                  95

Ile Glu Tyr Tyr Gln Lys Ala Leu Glu Leu Asp Pro Asn Asn Ala Glu
            100                 105                 110

Ala Lys Gln Asn Leu Gly Asn Ala Lys Gln Lys Gln Gly
        115                 120                 125

<210> SEQ ID NO 2
<211> LENGTH: 13
<212> TYPE: PRT
<213> ORGANISM: Artificial sequence
<220> FEATURE:
<223> OTHER INFORMATION: Sythetic

<400> SEQUENCE: 2

Ala His Ile Val Met Val Asp Ala Tyr Lys Pro Thr Lys
1               5                   10

<210> SEQ ID NO 3
<211> LENGTH: 320
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(10)
<223> OTHER INFORMATION: HIS tag
<220> FEATURE:
<221> NAME/KEY: MISC_FEATURE
<222> LOCATION: (12)..(12)
<223> OTHER INFORMATION: Inserted cysteine
<220> FEATURE:
<221> NAME/KEY: MISC_FEATURE
<222> LOCATION: (319)..(319)
<223> OTHER INFORMATION: Inserted cysteine

<400> SEQUENCE: 3

Met Ser Tyr Tyr His His His His His His Ser Cys Ser Asp Tyr Asp
1               5                   10                  15

Ile Pro Thr Thr Glu Asn Leu Tyr Phe Gln Gly Ala Met Gly Ser Ala
                20                  25                  30

Glu Ala Trp Tyr Asn Leu Gly Asn Ala Tyr Tyr Lys Gln Gly Asp Tyr
            35                  40                  45

Asp Glu Ala Ile Glu Tyr Tyr Gln Lys Ala Leu Glu Leu Asp Pro Arg
            50                  55                  60

Ser Ala Glu Ala Trp Tyr Asn Leu Gly Asn Ala Tyr Tyr Lys Gln Gly
 65                  70                  75                  80

Asp Tyr Asp Glu Ala Ile Glu Tyr Tyr Gln Lys Ala Leu Glu Leu Asp
                     85                  90                  95

Pro Arg Ser Ala Glu Ala Trp Tyr Asn Leu Gly Asn Ala Tyr Tyr Lys
                100                 105                 110

Gln Gly Asp Tyr Asp Glu Ala Ile Glu Tyr Tyr Gln Lys Ala Leu Glu
            115                 120                 125

Leu Asp Pro Arg Ser Ala Glu Ala Trp Tyr Asn Leu Gly Asn Ala Tyr
        130                 135                 140

Tyr Lys Gln Gly Asp Tyr Asp Glu Ala Ile Glu Tyr Tyr Gln Lys Leu
145                 150                 155                 160

Glu Leu Asp Pro Arg Ser Ala Glu Ala Trp Tyr Asn Leu Gly Asn Ala
                165                 170                 175

Tyr Tyr Lys Gln Gly Asp Tyr Asp Glu Ala Ile Glu Tyr Tyr Gln Lys
            180                 185                 190

Ala Leu Glu Leu Asp Pro Arg Ser Ala Glu Ala Trp Tyr Asn Leu Gly
        195                 200                 205

Asn Ala Tyr Tyr Lys Gln Gly Asp Tyr Asp Glu Ala Ile Glu Tyr Tyr
210                 215                 220

Gln Lys Ala Leu Glu Leu Asp Pro Arg Ser Ala Glu Ala Trp Tyr Asn
225                 230                 235                 240

Leu Gly Asn Ala Tyr Tyr Lys Gln Gly Asp Tyr Asp Glu Ala Ile Glu
                245                 250                 255

Tyr Tyr Gln Lys Ala Leu Glu Leu Asp Pro Arg Ser Ala Glu Ala Trp
            260                 265                 270

Tyr Asn Leu Gly Asn Ala Tyr Tyr Lys Gln Gly Asp Tyr Asp Glu Ala
        275                 280                 285

Ile Glu Tyr Tyr Gln Lys Ala Leu Glu Leu Asp Pro Arg Ser Ala Glu
290                 295                 300

Ala Lys Gln Asn Leu Gly Asn Ala Lys Gln Lys Gln Gly Ser Cys Ser
305                 310                 315                 320

<210> SEQ ID NO 4
<211> LENGTH: 69
<212> TYPE: PRT
<213> ORGANISM: Artificial sequence
<220> FEATURE:
<223> OTHER INFORMATION: Synthetic

<400> SEQUENCE: 4

Gly Ser Ala Glu Ala Trp Tyr Asn Leu Gly Asn Ala Tyr Tyr Gln Gly
 1               5                  10                  15

Asp Tyr Asp Glu Ala Ile Glu Tyr Tyr Gln Lys Ala Leu Glu Leu Asp
             20                  25                  30

Pro Arg Ser Ala Glu Ala Trp Tyr Asn Leu Gly Asn Ala Tyr Tyr Lys
         35                  40                  45

Gln Gly Asp Tyr Asp Glu Ala Ile Glu Tyr Tyr Gln Lys Ala Leu Glu
     50                  55                  60

Leu Asp Pro Arg Ser
 65

<210> SEQ ID NO 5

```
<211> LENGTH: 68
<212> TYPE: PRT
<213> ORGANISM: Artificial sequence
<220> FEATURE:
<223> OTHER INFORMATION: Synthetic

<400> SEQUENCE: 5

Gly Ser Ala Glu Ala Tyr Tyr Asn Leu Gly Asn Ala Tyr Tyr Gln Gly
1               5                   10                  15

Asp Tyr Asp Glu Ala Ile Glu Tyr Tyr Gln Lys Ala Leu Glu Leu Tyr
            20                  25                  30

Pro Arg Ser Ala Glu Ala Trp Tyr Asn Leu Gly Asn Ala Tyr Tyr Lys
        35                  40                  45

Gln Gly Asp Tyr Asp Glu Ala Ile Glu Tyr Tyr Gln Lys Ala Leu Glu
    50                  55                  60

Leu Asp Pro Arg
65
```